(12) United States Patent
Zheng et al.

(10) Patent No.: US 9,567,312 B2
(45) Date of Patent: Feb. 14, 2017

(54) CABAZITAXEL, RELATED COMPOUNDS AND METHODS OF SYNTHESIS

(71) Applicants: Shanghai Bioman Pharma Limited, Shanghai (CN); BN Pharmaceuticals Inc., Burnaby (CA)

(72) Inventors: Yunman Zheng, Shanghai (CN); Tianhui Xu, Shanghai (CN); Ragina Naidu, Burnaby (CA)

(*) Notice: Subject to any disclaimer, the term of this patent is extended or adjusted under 35 U.S.C. 154(b) by 0 days.

(21) Appl. No.: 14/351,963

(22) PCT Filed: Oct. 19, 2012

(86) PCT No.: PCT/EP2012/070773
§ 371 (c)(1),
(2) Date: Apr. 15, 2014

(87) PCT Pub. No.: WO2013/057260
PCT Pub. Date: Apr. 25, 2013

(65) Prior Publication Data
US 2014/0371474 A1   Dec. 18, 2014

(30) Foreign Application Priority Data

Oct. 19, 2011  (CN) .......................... 2011 1 0318046

(51) Int. Cl.
*C07D 305/00* (2006.01)
*C07D 305/14* (2006.01)
(52) U.S. Cl.
CPC .................................. *C07D 305/14* (2013.01)

(58) Field of Classification Search
CPC ............................. C07D 305/06; C07D 305/08
USPC ..................................... 549/511, 510
See application file for complete search history.

(56) References Cited

U.S. PATENT DOCUMENTS 5,556,877 A * 9/1996 Bouchard et al. ............ 514/449
2012/0149925 A1   6/2012 Kung et al.

FOREIGN PATENT DOCUMENTS

| CN | 102408397 A | 6/2012 |
|----|-------------|--------|
| WO | 9734866 | 9/1997 |
| WO | 20100024762 | 3/2010 |
| WO | 20100123186 | 10/2010 |

OTHER PUBLICATIONS

International Search Report and Written Opinion for related PCT/EP2012/070773, dated Dec. 12, 2012.
Ojima, et al., A Highly Efficient Route to Taxotere by the β-Lactam Synthon Method, Tetrahedron Letters, vol. 34, No. 26, pp. 4149-4152, 1993.
Johnson, et al., Taxol Chemistry, 7-O-Triflates as Precursors to Olefins and Cyclopropanes, Tetrahedron Letters, vol. 35, No. 43, pp. 7893-7896, 1994.

(Continued)

*Primary Examiner* — T. Victor Oh
(74) *Attorney, Agent, or Firm* — Calfee, Halter & Griswold LLP

(57) ABSTRACT

The invention provides new cabazitaxel isoserine ester intermediates and new synthetic methods, and a preparation method for the anti-tumour drugs cabazitaxel, docetaxel and paclitaxel from the new cabazitaxel isoserine intermediates.

7 Claims, 5 Drawing Sheets (continued)

(56) References Cited

OTHER PUBLICATIONS

Chen, et al., The Chemistry of Taxanes: Reaction of Taxol and Baccatin Derivatives With Lewis Acids in Aprotic and Protic Media, Tetrahedron Letters, vol. 48, No. 14, pp. 2805-2828, 1993.

Dubois, et al., Conformation of Taxotere® and Analogues Determined by NMR Spectroscopy and Molecular Modeling Studies; Tetrahedron vol. 49, No. 30, pp. 6533-6544, 1993.

Kanazawa, et al., Highly Stereocontrolled and Efficient Preparation of the Protected, Esterification-Ready Docetaxel (Taxotere) Side Chain; J. Org. Chem. 1994, 59, 1238-1240.

Du, et al., Synthesis and Evaluation of Water-Soluble Docetaxel Prodrugs-Docetaxel Esters of Malic Acid; Bioorganic & Medicinal Chemistry 15 (2007) pp. 6323-6330.

Guenard, et al., Effects of the Hydrophobicity of Taxoids on their Interaction with Tubulin; Bioorganic & Medicinal Chemistry 8 (2000) pp. 145-156.

Georg, et al., Selective C-2 and C-4 Deacylation and Acylation of Taxol: The First Synthesis of a C-4 Substituted Taxol Analogue; 134a Tetrahedron Letters, 35 (Nov. 28, 1994) No. 48, Kidlington, Oxford GB.

* cited by examiner

CABAZITAXEL, RELATED COMPOUNDS AND METHODS OF SYNTHESIS

CROSS REFERENCE TO RELATED APPLICATIONS

This application is the U.S. national stage entry of PCT/EP2012/070773, with an international filing date of 19 Oct. 2012, which is hereby incorporated by reference herein in its entirety and which claims priority to and any other benefit of Chinese Application Serial No. 201110318046.4, with a filing date of 19 Oct. 2011, which is hereby incorporated by reference herein in its entirety.

DESCRIPTION OF THE INVENTION

This invention relates to chemical synthesis of compounds having utility in the medical field. In particular the invention provides a preparation method of a novel taxane isoserine esters and novel methods of preparation of the anti-tumor drug cabazitaxel.

BACKGROUND TECHNOLOGY

The taxane family of terpenes has received much attention in the scientific and medical community, because members of this family have demonstrated broad spectrum of anti-leukemic and tumor-inhibitory activity. A well-known member of this family is paclitaxel (Taxol®).

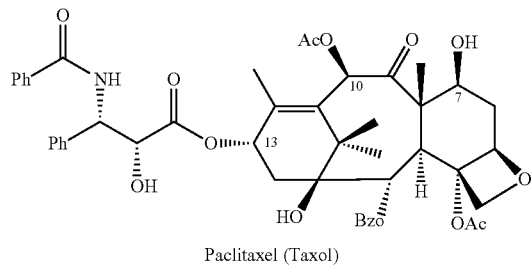

Paclitaxel (Taxol)

Paclitaxel was first isolated from the bark of the pacific yew tree (*Taxus brevifolia*) in 1971, and has proved to be a potent natural anti-cancer agent. To date, paclitaxel has been found to have activity against different forms of leukemia and against solid tumors in the breast, ovary, brain, and lung in humans.

As will be appreciated, this beneficial activity has stimulated an intense research effort over recent years with a view to identifying other taxanes having similar or improved properties, and with a view to developing synthetic pathways for making these taxanes, such as paclitaxel.

This research effort led to the discovery of a synthetic analogue of paclitaxel, namely, docetaxel (also known as Taxotere®). As disclosed in U.S. Pat. No. 4,814,470, docetaxel has been found to have a very good anti-tumour activity and better bioavailability than paclitaxel. Docetaxel is similar in structure to paclitaxel, having t-butoxycarbonyl instead of benzoyl on the amino group at the 3' position, and a hydroxy group instead of the acetoxy group at the C-10 position.

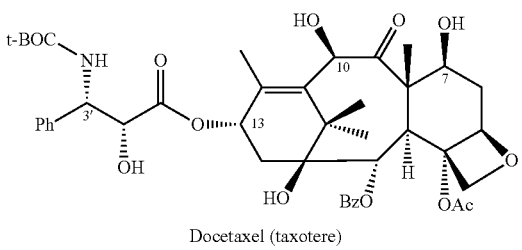

Docetaxel (taxotere)

As will be appreciated, taxanes are structurally complicated molecules, and the development of commercially viable synthetic methods to make taxanes has been a challenge. A number of semi-synthetic pathways have been developed over the years, which typically begin with the isolation and purification of a naturally occurring starting material, which can be converted to a specific taxane derivative of interest. Cabazitaxel (I) is an anti-tumor drug which belongs to the taxol family. It differs from docetaxel in that it has methoxy groups at positions 7 and 10 of the molecule, as opposed to the hydroxyl groups at equivalent positions in docetaxel. Cabazitaxel is obtained by semi-synthesis from an extract of Chinese yew (*Taxus mairei*). It is understood that cabazitaxel can be obtained via semi-synthesis from other *taxus* species including *T. candensis, T. baccatta, T. chinensis, T. mairei* etc.

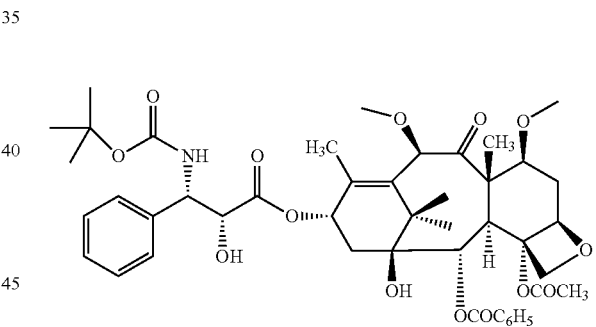

Cabazitaxel (I)

Cabazitaxel is a semi-synthetic derivative of the natural taxoid 10-deacetylbaccatin III (10-DAB) with potentially unique antineoplastic activity for a variety of tumors. Cabazitaxel binds to and stabilizes tubulin, resulting in the inhibition of microtubule depolymerization and cell division, cell cycle arrest in the G2/M phase, and the inhibition of tumor cell proliferation. This drug is a microtubule depolymerization inhibitor, which can penetrate blood brain barrier (BBB).

Cabazitaxel was recently approved by the US Federal Drug Administration (FDA) for the treatment of docetaxel resistant hormone refractory prostate cancer. It has been developed by Sanofi-Aventis under the trade name of Jevtana. The CAS number for the compound is 183133-96-2. A synonym is dimethoxydocetaxel. The compound is also known as RPR-116258A; XRP6258; TXD 258; and axoid XRP6258.

The free base form of cabazitaxel has the chemical name (2aR,4S,4aS,6R,9S,11S,12S,12aR,12bS)-12b-acetoxy-9-(((2R,3S)-3-((tert-butoxycarbonyl)amino)-2-hydroxy-3-phenylpropanoyl)oxy)-11-hydroxy-4,6-dimethoxy-4-a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-12-yl benzoate.

In a first part of this description, taxel drugs including paclitaxel (taxol), docetaxel (taxotere) and cabazitaxel may be prepared starting from 10-deacetylbaccatin (known as 10-DAB) derived from *Taxus* plants, via semi-synthesis. Furthermore, the same inventive methodologies can be used to semi-synthesize cabazitaxel starting from 9-dihydro-13-acetylbaccatin III (9-DHB).

Patent numbers CN1213042C, CN152870, CN1179716 and CN1179775 disclose methods to prepare cabazitaxel from 10-DAB (herein compound II).

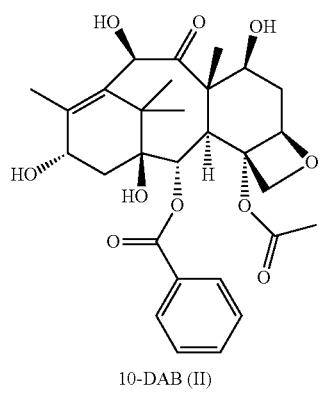 [SMILES: CC(=O)O[C@@]12CO[C@@H]1C[C@H](O)[C@@]1(C)C(=O)[C@H](O)C3=C(C)[C@@H](O)C[C@@](O)([C@@H](OC(=O)c4ccccc4)[C@H]21)C3(C)C]

10-DAB (II)

A typical prior art synthesis route is as follows:

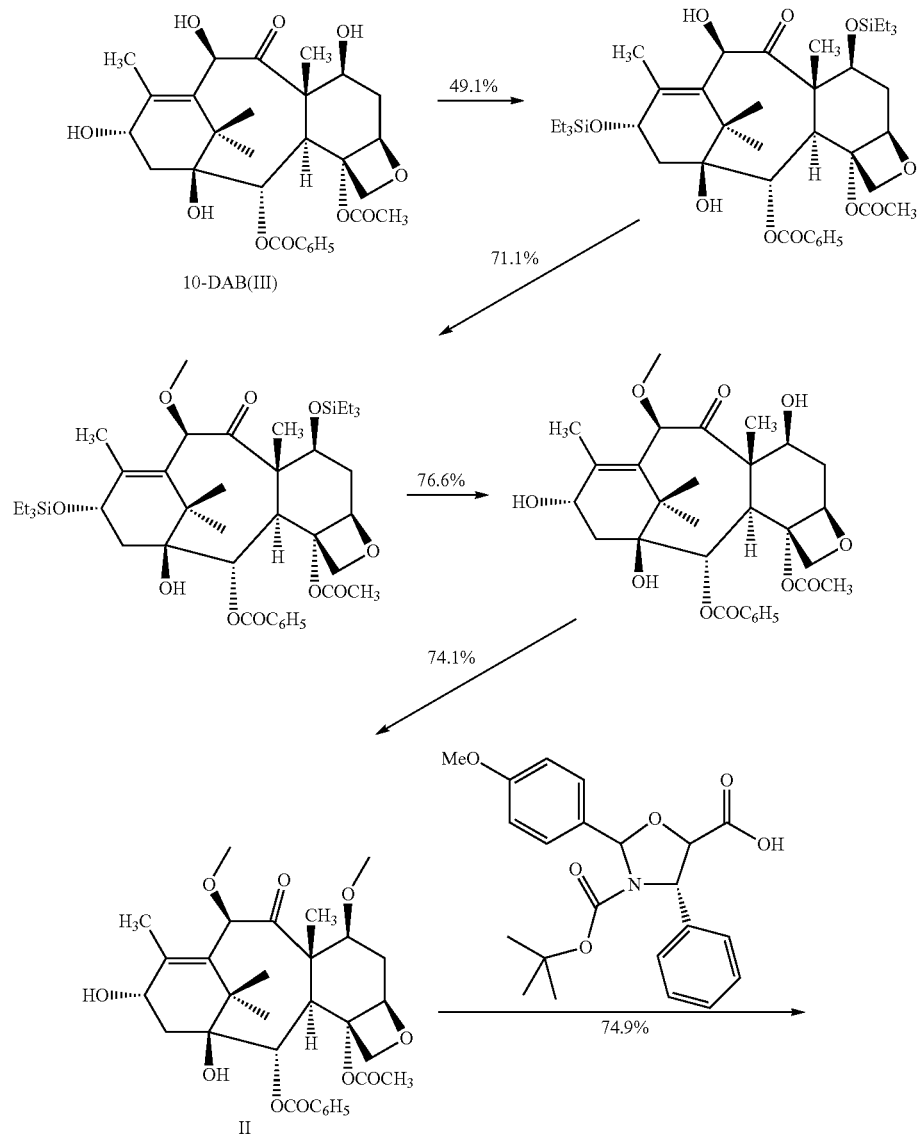

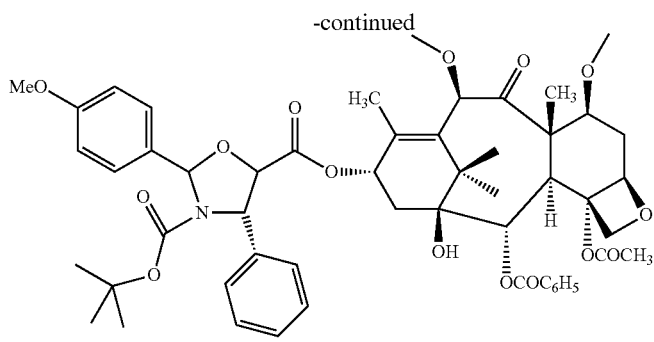

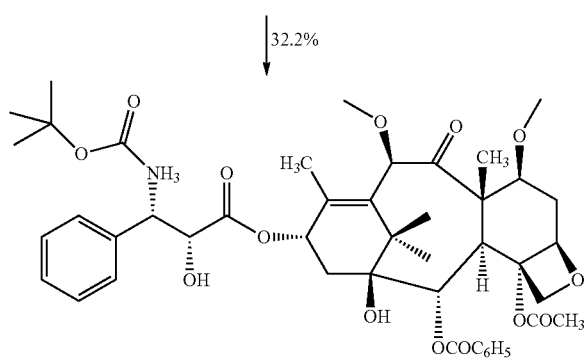

The method above which synthesizes cabazitaxel has many synthetic steps, a very low overall yield and high price.

There is therefore a need in the art to develop new methods to synthesize cabazitaxel and its intermediates to improve the yield of cabazitaxel, simplify the methodology and optimize the synthetic technology.

SUMMARY

According to the present invention, there is provided a compound having the following formula:

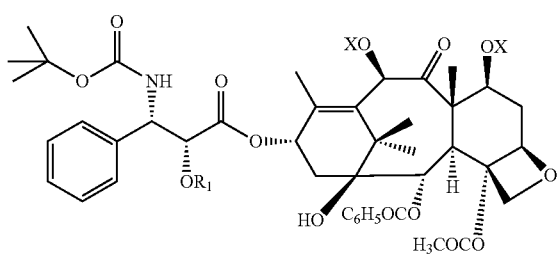

or a salt thereof, wherein R1 is a hydroxy protecting group and wherein each X is independently either hydrogen, trichloroethoxycarbonyl (TROC) or a straight chain or branched alkyl group, preferably selected from methyl, ethyl, propyl or butyl.

In one example of the invention, one or each X is H.

Alternatively one or each X is a straight chain or branched alkyl group, preferably selected from methyl, ethyl, propyl or butyl. Preferably one or each X is methyl.

Advantageously one or each X is trichloroethoxycarbonyl i.e. $CCl_3CH_2OC(O)$—.

Conveniently R1 is selected from the group consisting of benzyloxy-carbonyl, tert-butyloxy carbonyl, tri-chloro-acetyl, trifluoro-acetyl, 1-ethoxy-ethyl, methoxy-iso-propyl, tri-ethyl-silyl, tri-methyl-silyl, furanidinyl, tert-butyl-bi-methyl-silyl, tert-butyl-bi-phenyl-silyl.

Advantageously R1 is selected from the group consisting of 1-ethoxy-ethyl-, methoxyl-iso-propanyl-, tri-methyl-silyl-, furanidinyl- or tert-butyl-bi-methyl-silyl-.

The present invention also provides a method of preparing a taxane compound from a protected taxane intermediate having at least one protecting group, the method comprising reacting the protected taxane intermediate with a reducing agent and a Lewis acid to substitute the at least one protecting group with a hydroxyl group.

Preferably the protecting group is trichloroethoxycarbonyl (TROC).

Conveniently the reducing agent is selected from a metal including zinc, potassium, calcium, barium, sodium and magnesium and a metal hydride including NaH, LiH, $LiAlH_4$ and $CaH_2$, preferably in powder form.

Advantageously the reducing agent is zinc, for example zinc metal powder.

Conveniently the Lewis acid is selected from ammonium chloride, ammonium sulphate, ammonium acetate, zinc chloride, magnesium chloride, calcium chloride and aluminum chloride.

Preferably the Lewis acid is ammonium chloride or magnesium chloride.

Advantageously the method is carried out in a polar solvent.

Conveniently the polar solvent is selected from water, alcohol, acetone, tetrahydrofuran, acetonitrile and mixtures thereof.

Preferably the polar solvent is selected from methanol, ethanol, acetone and mixtures thereof.

The protected taxane intermediate can have the formula V:

V

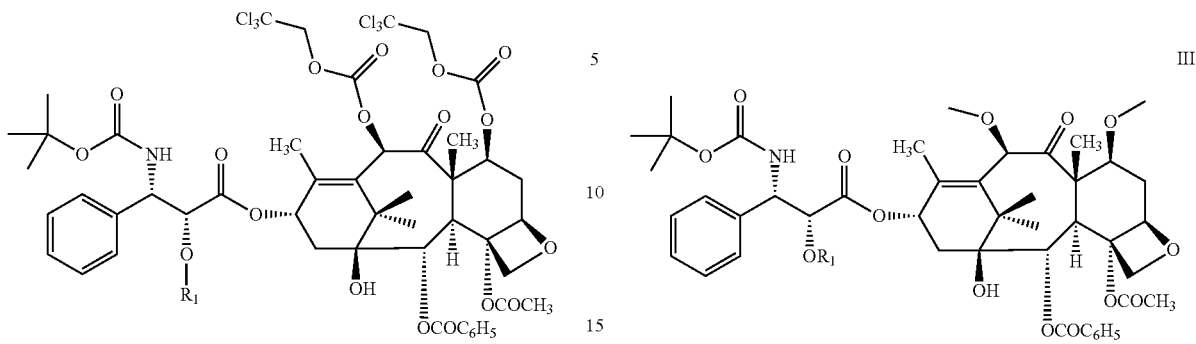

in which case the corresponding taxane compound has the formula IV,

IV

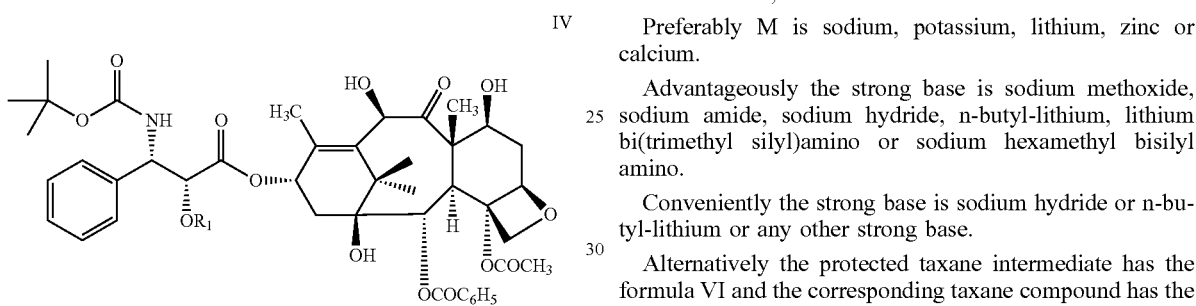

wherein R1 is a hydroxy protecting group.

The inventive method can further comprise:
a. reacting the a taxane compound of formula IV

IV

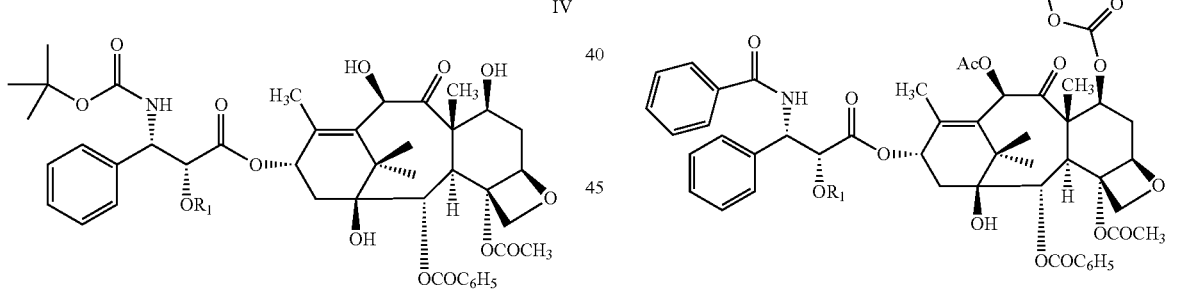

with a strong base to obtain a corresponding metallated compound VI

VI

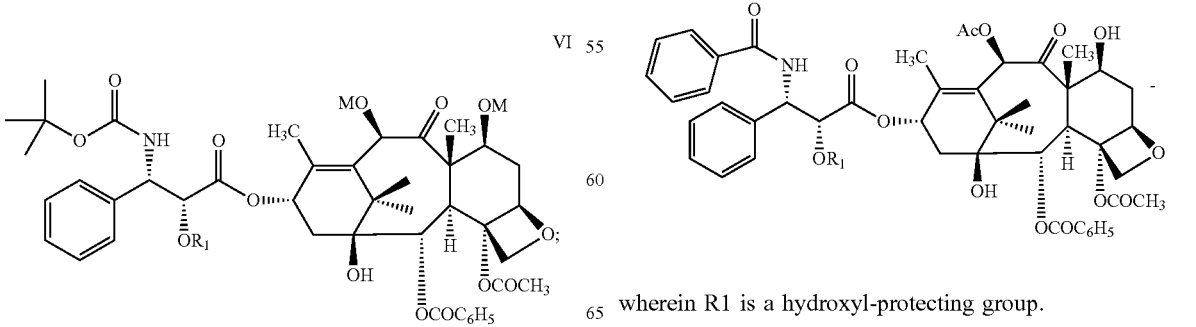

b) and reacting with methyl iodide or dimethyl sulphate to obtain compound III;

III

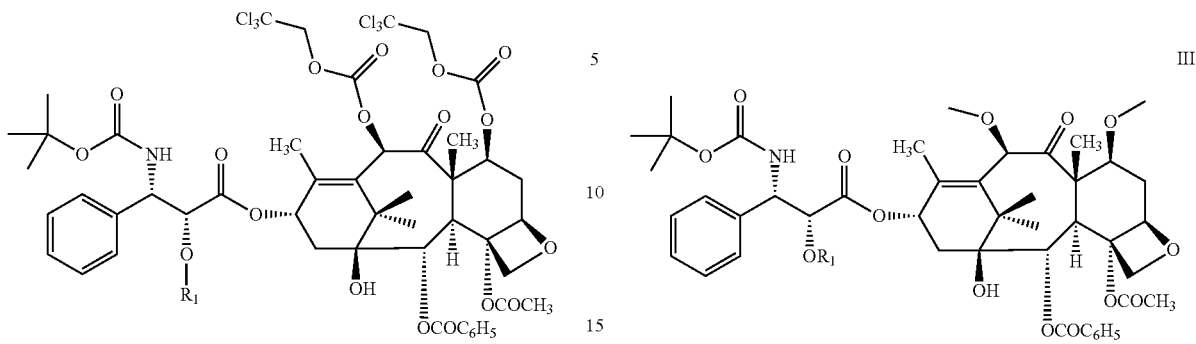

wherein R1 is hydroxy protecting group; and
M is a IA, IIA, IIIA, IVA, VA, VIA group element, or a transition metal, zinc or calcium.

Preferably M is sodium, potassium, lithium, zinc or calcium.

Advantageously the strong base is sodium methoxide, sodium amide, sodium hydride, n-butyl-lithium, lithium bi(trimethyl silyl)amino or sodium hexamethyl bisilyl amino.

Conveniently the strong base is sodium hydride or n-butyl-lithium or any other strong base.

Alternatively the protected taxane intermediate has the formula VI and the corresponding taxane compound has the formula VII:

VI

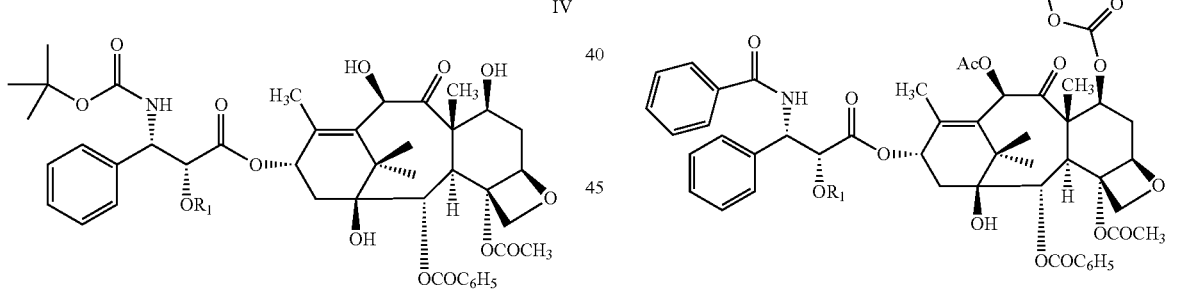

VII

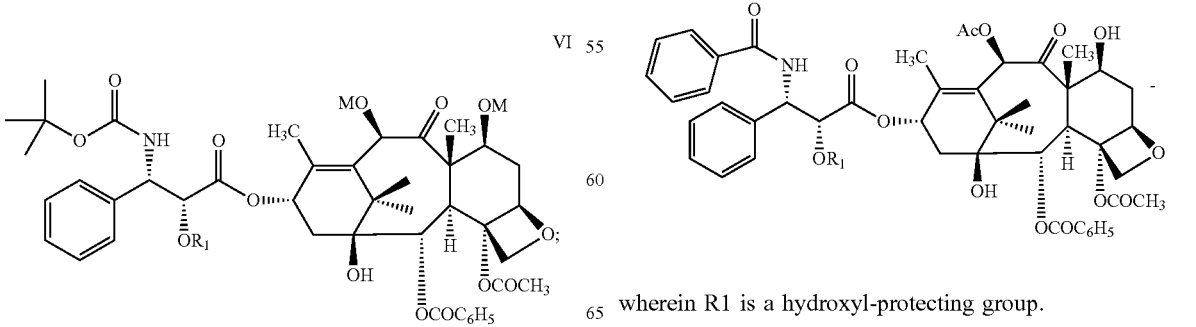

wherein R1 is a hydroxyl-protecting group.

Conveniently the method may further comprise deprotecting the R1 protecting group from compound III

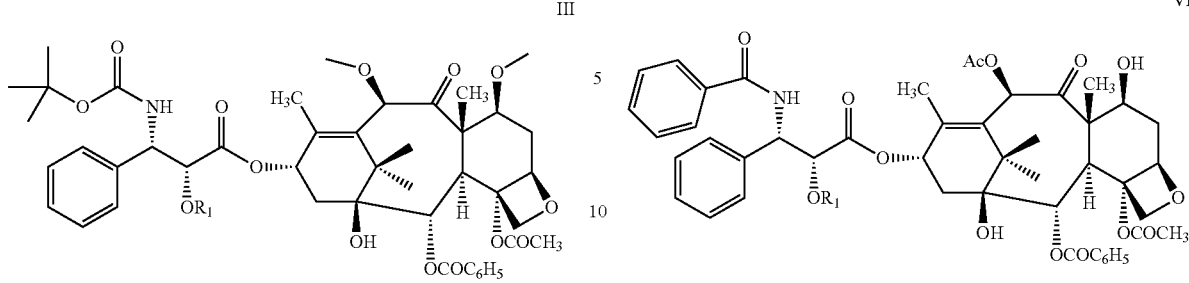

to obtain cabazitaxel to obtain paclitaxel

Conveniently the method may alternatively further comprise deprotecting the R1 protecting group from compound IV

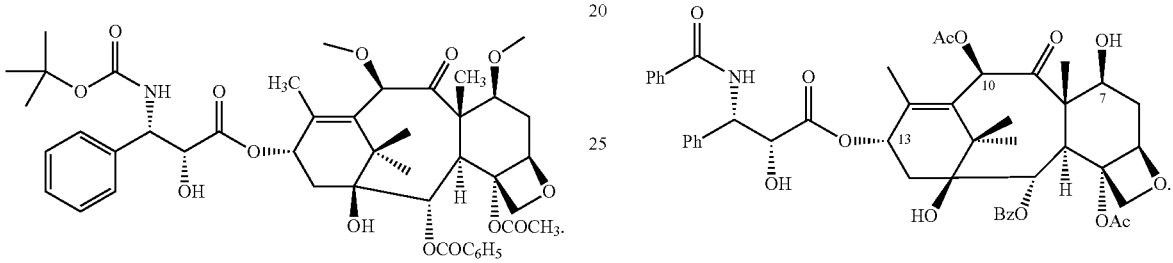

to obtain docetaxel

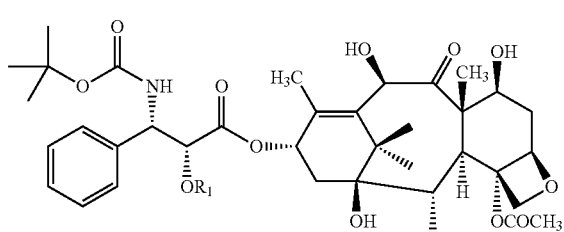

Conveniently the method may alternatively further comprise deprotecting the R1 protecting group from compound VII Preferably the method is carried out by deprotecting the protecting group R1 in acid solvent, the acid being selected from formic acid, acetic acid, hydrofluoric acid, hydrochloric acid, p-methyl-benzene monosulfonic acid or a mixture thereof, wherein the solvent is water, organic solvent or organic solvent with water.

Advantageously the acid is hydrochloric acid or hydrofluoric acid.

Conveniently R1 is selected from the group consisting of benzyloxy-carbonyl, tert-butyloxy-carbonyl, tri-chloro-acetyl, tri-fluoro-acetyl, 1-ethoxy-ethyl, methoxy-iso-propanyl, tri-ethyl-silyl or tri-methyl-silyl, furanidinyl, tert-butyl-bi-methyl-silyl, tert-butyl-bi-phenyl-silyl.

Preferably R1 is selected from the group consisting of 1-ethoxy-ethyl-, methoxy-iso-propanyl, tri-ethyl-silyl-, furanidinyl or tert-butyl-bi-methyl-silyl.

The present invention also provides the use of compound III in the preparation of cabazitaxel

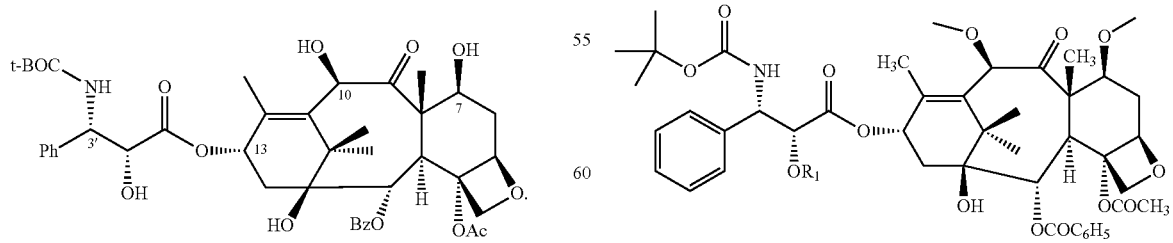

The present invention also provides the use of use of compound IV in the preparation of cabazitaxel and docetaxel.

IV

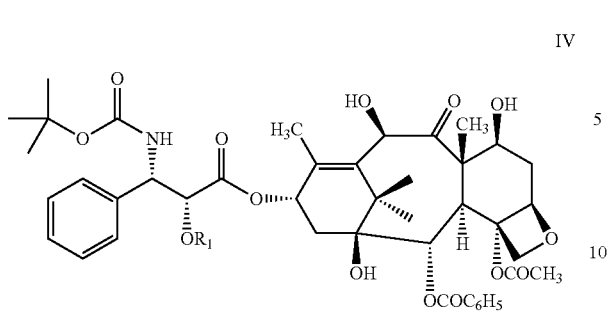

The present invention also provides the use of use of a compound defined in the claims in the preparation of a taxane.

There is also provided a method for preparing a taxane product, the method comprising:

a. Providing a taxane starting material having the general formula:

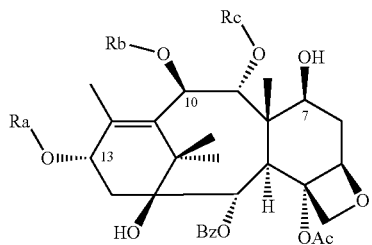

in which Ra and Rb are the same or are different and are selected from hydrogen or a hydroxyl protecting group, and in which Rc is either hydrogen or represents a second bond back to carbon C9 thereby providing a =O group at C9;

b. Protecting the C7 hydroxyl group with a protecting group;

c. Removing the hydroxyl protecting groups at positions 10 and 13, and replacing with hydroxyl groups, if hydroxyl groups are not already present at C10 and C13;

d. Oxidising at the 9 position to provide a =O at C9, if a =O group is not already present at C9;

e. Coupling with an R1-protected phenylisoserine side chain precursor compound to provide a protected taxane intermediate compound;

f. Optionally further protecting the C10 hydroxy group either before or after coupling step (e); and g. Performing the method of any one of claims 8 to 29.

Preferably the taxane starting material is a taxoid selected from 9DHB or 10DAB:

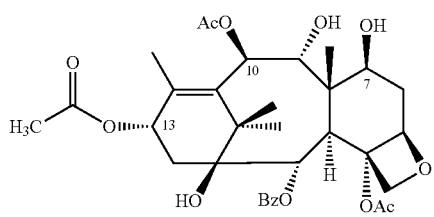

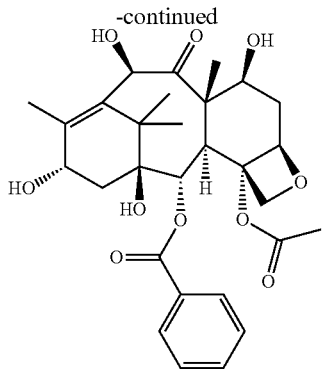

Advantageously the C7 and C10 protecting group are independently selected from trichloroethoxycarbonyl and alkyl groups.

Further features of the invention are set out in the following numbered clauses:

1. A compound according to formula IV and its salts, wherein R1 is a hydroxy protecting group.

2. The compound of clause 1 wherein R1 of formula IV is benzyloxy-carbonyl, tert-butyloxy carbonyl, tri-chloro-acetyl, trifluoro-acetyl, 1-ethoxy-ethyl, methoxy-iso-propyl, tri-ethyl-silyl, tri-methyl-silyl, furanidinyl, tert-butyl-bi-methyl-silyl, tert-butyl-bi-phenyl-silyl.

3. The compound of clause 2 wherein R1 of formula IV is 1-ethoxy-ethyl-, methoxy-iso-propanyl-, tri-methyl-silyl-, furanidinyl- or tert-butyl-bi-methyl-silyl-.

4. A compound according to formula III and its salts, wherein R1 is a hydroxy protecting group.

5. The compound of clause 4 wherein R1 of formula III is: benzoxyl-carbonyl, tert-butyloxy carbonyl, tri-chloro-acetyl, tri-fluoro-acetyl, 1-ethoxy-ethyl-, methoxy-iso-propanyl-, tri-ethyl-silyl- or tri-methyl-silyl-, furanidinyl, tert-butyl-bi-methyl-silyl-, tert-butyl-bi-phenyl-silyl-.

6. The compound of clause 5 wherein R1 of formula III is: 1-ethoxy-ethyl-, methoxy-iso-propanyl-, tri-methyl-silyl-, furanidinyl or tert-butyl-bi-methyl-silyl.

7. A method for preparing a compound of formula IV including de-protection of tri-chloro-carbonyl of compound V to obtain compound IV, wherein R1 of formula V is a hydroxy protecting group.

8. The method of clause 7 wherein R1 of formula V is: benzyloxy-carbonyl, tert-butyloxy-carbonyl, tri-chloro-acetyl, tri-fluoro-acetyl, 1-ethoxy-ethyl, methoxy-iso-propanyl, tri-ethyl-silyl or tri-methyl-silyl, furanidinyl, tert-butyl-bi-methyl-silyl, tert-butyl-bi-phenyl-silyl.

9. The method of clause 8 wherein R1 of formula V is 1-ethoxy-ethyl-, methoxy-iso-propanyl, tri-ethyl-silyl-, furanidinyl or tert-butyl-bi-methyl-silyl.

10. The method of any of clauses 7 to 9 wherein the deprotection uses zinc powder and a Lewis acid, in polar solvent, in a reduction reaction to de-protect tri-chloro-methoxy-carbonyl selectively.

11. The method of clause 10 wherein the Lewis acid is selected from ammonium chloride, ammonium sulphate, ammonium acetate, zinc chloride, magnesium chloride, calcium chloride and aluminum chloride.

12. The method of clause 11 wherein the mentioned Lewis acid is ammonium chloride or magnesium chloride.

13. The method of clause 10 wherein the polar solvent is water, lower alkyl alcohol, acetone, furanidine and acetonitrile.

14. The method of clause 13 wherein the polar solvent is methanol, ethanol and acetone.
15. A method for preparing compound III including:
  1) Reacting compound IV with a strong base to obtain compound IV's metallated equivalent compound VI
  2) Reacting compound VI with methyl iodide or dimethyl sulphate to obtain compound III;
  Wherein R1 is a hydroxyl protecting group;
  M is IA, IIA, IIIA, IVA, VA, VIA group elements, or transition metals, zinc or calcium.
16. The method of clause 15 wherein R1 is: benzyloxy-carbonyl, tert-butyloxy-carbonyl, tri-chloro-acetyl, tri-fluoro-acetyl, 1-ethoxy-ethyl, methoxy-iso-propanyl, tri-ethyl-silyl or tri-methyl-silyl, furanidinyl, tert-butyl-bi-methyl-silyl, tert-butyl-bi-phenyl-silyl.
17. The method of clause 16 wherein R1 is 1-ethoxy-ethyl, methoxy-iso-propanyl, tri-ethyl-silyl, furanidinyl or tert-butyl-bi-methyl-silyl.
18. The method of clause 15 wherein M of compound VI is sodium, potassium, lithium, zinc or calcium.
19. The method of clause 15 wherein the strong base is sodium methoxide, sodium amide, sodium hydride, n-butyl-lithium, lithium bi(trimethyl silyl)amino or sodium hexamethyl bisilyl amino.
20. The method of clause 19 wherein the strong base is sodium hydride or n-butyl-lithium.
21. A method of deprotecting tri-chloro-ethoxy-carbonyl selectively during a reaction to obtain cabazitaxel, in which with the presence of zinc powder and Lewis acid, in polar solvent, the reducing reaction deprotects tri-chloro-ethoxy-carbonyl.
22. The method of clause 21 wherein the Lewis acid is ammonium chloride, ammonium sulphate, ammonium acetate, zinc chloride, magnesium chloride, calcium chloride and aluminum chloride.
23. The method of clause 22 wherein the Lewis acid is ammonium chloride or ammonium sulphate.
24. The method of clause 21 wherein the polar solvent is water, lower alkyl alcohol, acetone, furanidine or acetonitrile.
25. The method of clause 24 wherein the lower alkyl alcohol mentioned is methanol, ethanol or propanol.
26. A method of cabazitaxel preparation including: deprotecting the R1 protecting group from compound II to obtain cabazitaxel.
27. The method of clause 26 comprising deprotecting the protecting group in acid solvent, the acid is formic acid, acetic acid, hydrofluric acid, hydrochloric acid, p-methyl-benzene monosulfonic acid or their mixture and the solvent is water, organic solvent or organic solvent with water.
28. The method of clause 27 wherein the acid is hydrochloric acid or hydrofluoric acid.
29. A method of preparation of docetaxel including deprotecting the protecting group R1 from compound IV to obtain docetaxel.
30. The method of clause 29 comprising deprotecting the protecting group in acid solvent, the acid is formic acid, acetic acid, hydrofluoric acid, hydrochloric acid, p-methyl benzene monosulfonic acid or their mixture, the solvent is water, organic solvent or organic solvent with water.
31. The method of clause 30 wherein the acid is hydrochloric acid or hydrofluoric acid.
32. A method of taxol preparation including the following steps: (1) deprotect tri-chloro-ethoxy-carbonyl from compound VI to obtain compound VII; and (2) deprotect the protecting group R1 from compound VII to obtain taxol; wherein R1 is hydroxyl-protecting group.
33. The method of clause 32 in the presence of zinc powder and Lewis acid in polar solvent wherein the reducing reaction deprotects tri-chloro-ethoxy-carbonyl selectively.
34. The method of clause 33 wherein the Lewis acid is ammonium chloride, ammonium sulfate, ammonium acetate, zinc chloride, calcium chloride and aluminum chloride.
35. The method of clause 34 wherein the Lewis acid is ammonium chloride or ammonium sulfate.
36. The method of clause 33 wherein the polar solvent is water, lower alkyl alcohol, acetone, furanidine and acetonitrile.
37. The method of clause 36 wherein the polar solvent is methanol, ethanol or acetone.
38. Application of compound III in the preparation of cabazitaxel.
39. Application of compound IV in the preparation of cabazitaxel and docetaxel.

DETAILED DESCRIPTION

The invention provides a new method for the preparation of cabazitaxel, one embodiment of which can be summarized as follows, showing the preparation of a protected taxane intermediate and its deprotection to taxane compounds:

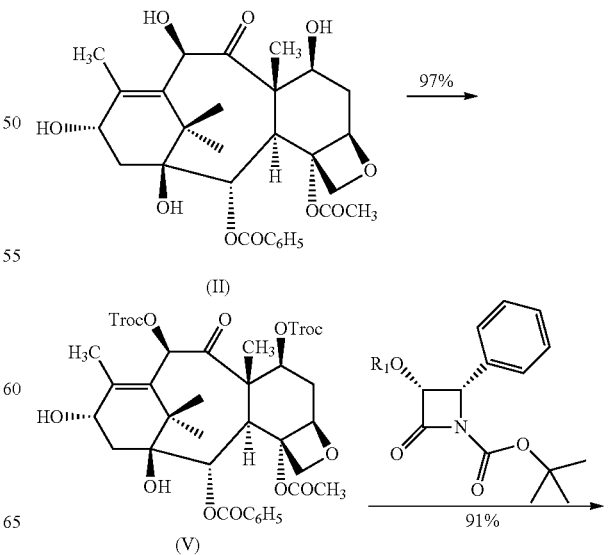

Figure 1:
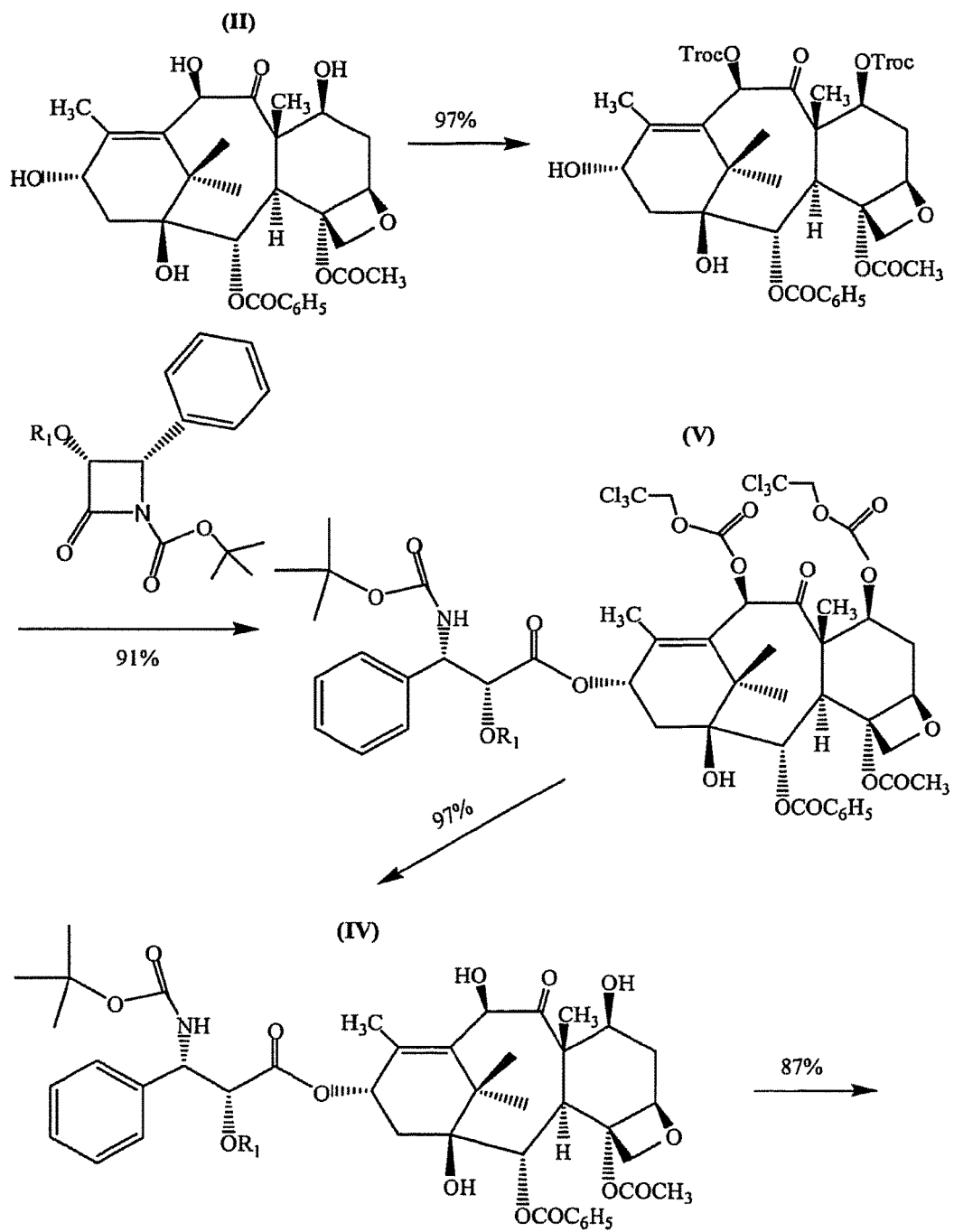
FIG. 1 depicts a first method of preparing cabazitaxel according to the invention.
Figure 1:
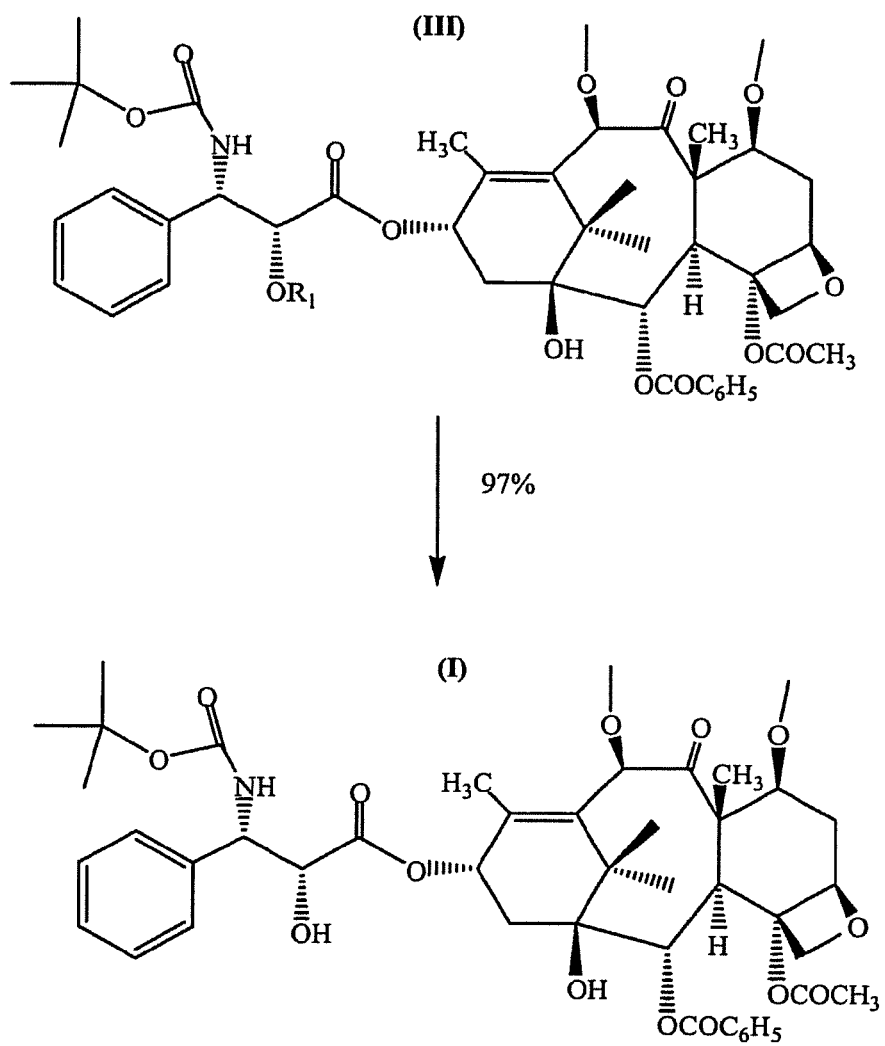

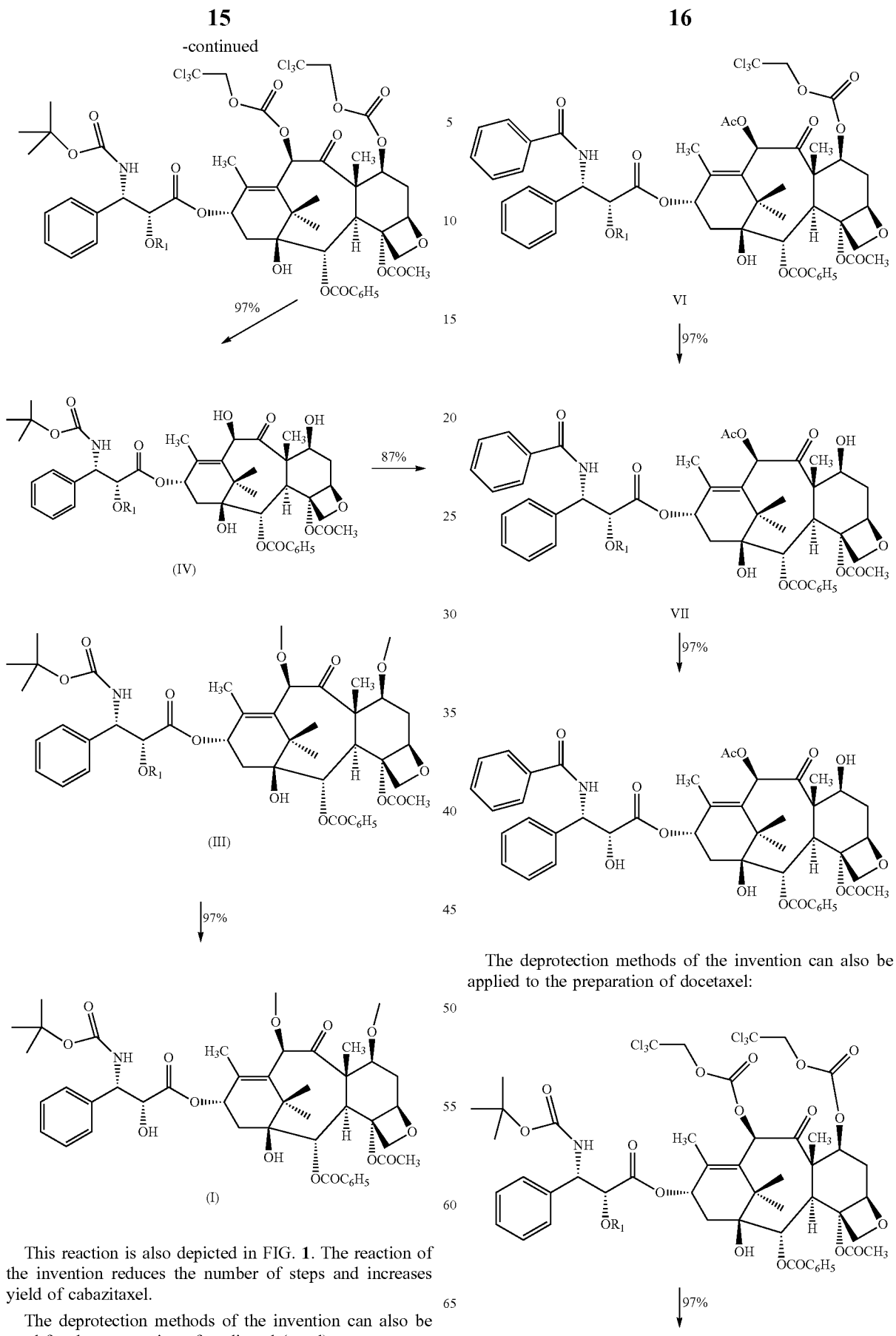
This reaction is also depicted in FIG. 1. The reaction of the invention reduces the number of steps and increases yield of cabazitaxel.
The deprotection methods of the invention can also be used for the preparation of paclitaxel (taxol):
The deprotection methods of the invention can also be applied to the preparation of docetaxel:

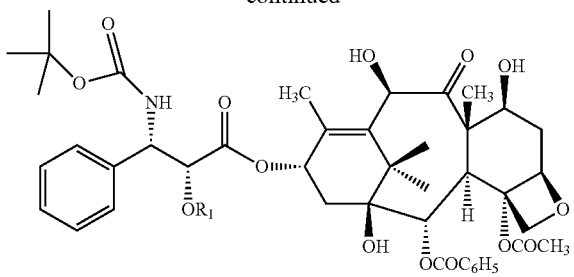

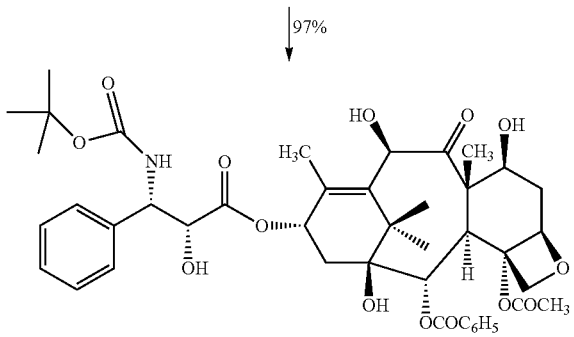

10-DAB Synthetic Routes

A first synthetic pathway of the invention can be summarized as follows, as illustrated above, wherein steps (a) and (b) are known in the art for example from WO 2006/004708, WO 2008/032104 and EP 2 003 124 A1.

a) Starting from 10-DAB (compound II), selectively protect the 7 and 10 positions of the molecule with an OH-protecting group such as TROC (trichloroethoxycarbonyl groups);
b) Couple the protected 10-DAB analogue at the 13 position to a phenylisoserine side-chain precursor (a beta-lactam) protected by a suitable hydroxy protecting group R1 at the 2'-position such that the resulting 7,10-protected C-13 substituted taxane intermediate (compound V) has an R1 hydroxy protecting group at the 2'-position on the phenylisoserine side chain;
c) Deprotect at the 7 and 10 positions using a reducing agent and a Lewis acid to yield 7,10-hydroxy compound (IV);
d) Methylate at the 7 and 10 positions to provide novel ester III; and
e) Deprotect the R1 group to yield cabazitaxel (I).

To produce docetaxel, one simply needs to omit the methylation step (d) above, since docetaxel is a hydroxy analogue of cabazitaxel.

Processes for the side-chain condensation reaction have been described in the art, for example in WO 2008/090368 and WO2004033442. Such techniques are suitable for the side-chain addition reactions mentioned herein and depicted in the reaction schemes of this disclosure.

Paclitaxel may also be produced using the same methodology, starting from 9-dihydro-13-acetylbaccatin III (9-DHB) instead of 10-DAB and noting that just one selective protection is necessary at step a.

An important intermediate of the above synthetic pathways is the novel taxol isoserine ester or its salt (formula III):

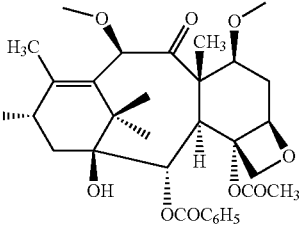

In compound III, the moiety R1 is hydroxy (or hydroxyl) protecting group.

The hydroxy protecting group is any group which can protect hydroxy. It should be a group that remains stable during reaction and after reaction, and can be removed to deprotect without destroying any other structure of the molecule. These kinds of group can be found in the following reference "The protecting groups in organic synthesis" (T. W. Greene, East China University of Science & Technology publisher) and "Protecting groups" (P. Kocienski, Thieme Publisher). In this invention, the hydroxy protecting group can be any hydroxy protecting group, as understood by a skilled person.

In the method of the invention, R1 is a hydroxy protecting group which can be deprotected in acidic, basic or neutral pH.

In an example at the invention, R1 is benzyloxy-carbonyl, tert-butyloxy-carbonyl, trichloro-acetyl, trifluoro-acetyl, 1-ethoxy-ethyl, methoxy-iso-propanyl, tri-ethylsilyl (TES), or trimethyl silyl (TMS), furanidinyl, tert-butyl-bimethylsilyl (TBS), tert-butyl-biphenylsilyl (TBDIPS), optimal protecting group is 1-ethoxy-ethyl (EE), tri-ethylsilyl (TES), tetrahydropyrane (THP) or tert-butyl-bimethyl silyl (TBS).

A further important novel taxel isoserine ester or its salt, involved as an intermediate in the methodologies of the invention, has the compound number IV:

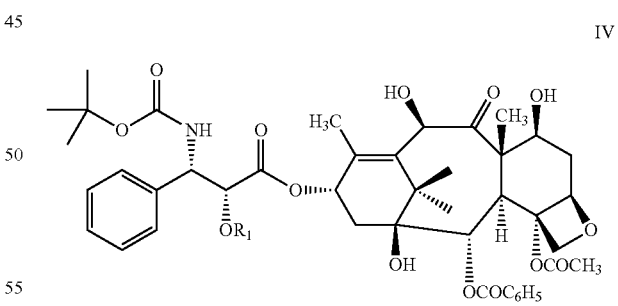

R1 is the hydroxyl protecting group mentioned above for compound III.

Preparation of Compound IV (Step c Above)

Compound IV can be obtained in the art by zinc powder reduction methods to selectively deprotect the trichloroethoxycarbonyl groups (TROC groups) from compound V. Preparation of compound V can be found in the reference Bioorganic & Medicinal Chemistry Letters, Vol 13, No. 11, 2419-2482, 1993.

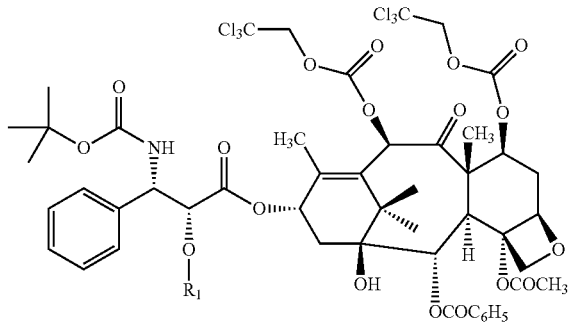

V

In formula V, R1 is a hydroxyl protecting group as outlined above for formula III, or hydrogen.

In the published reports, trichloroethoxycarbonyl (TROC) can be deprotected in the presence of zinc powder in acetic acid.

If R1 is more or less stable in acetic acid, then acetic acid deprotection may also be used to selectively deprotect trichloroethoxycarbonyl (TROC), for example when R1 is triethylsilyl, tert-butyl-bimethyl silyl (TBS) and tert-butyl-biphenyl silyl. However due to the presence of acetic acid, a small proportion of the protecting group at R1 is expected to also be deprotected. The yield of compound IV is therefore decreased and work-up of the reaction is difficult due to side products.

The invention provides a novel method to deprotect trichloroethoxycarbonyl (TROC).

In the invention, acetic acid is replaced by a Lewis acid and the solvent is preferably a polar solvent or solvent containing polarity. Under these conditions, R1 can be any hydroxyl protecting group, including acid-sensitive groups, such as tetrahydropyrone (THP) or 1-ethoxy-ethyl.

Polar solvents include but are not limited to all alcohols, acetone, tetrahydrofuran, acetonitrile and water.

The reducing agent can be any reducing agent known in the art, but preferably a metal-based reducing agent including metals such as zinc, potassium, calcium, barium, sodium and magnesium and metal hydrides such as NaH, LiH, LiAlH$_4$ and CaH$_2$. The reducing agent may be in the form of a powder.

A Lewis acid can be defined in the art as an electron pair (lone pair) acceptor, i.e. an entity that can accept a pair of electrons to complete its stable electronic configuration. Lewis acids include but are not limited to ammonium chloride, ammonium sulfate, ammonium acetate, zinc chloride, magnesium chloride and calcium chloride.

Optionally, the deprotection reaction can occur in a solvent containing lower alkyl alcohol or water in the presence of zinc powder and ammonium chloride. A lower alkyl alcohol, as defined in this specification, is a C1, C2, C3, C4 or C5 straight chain or branched alkyl alcohol such as methanol, ethanol or propanol.

The TROC deprotection reaction of the invention is typically carried out at −100 to 75 degrees C., preferably −10 to 50 degrees C. and more preferably 5 to 10 degrees C.

The reaction time for the invention can be 1 minute to 24 hrs, or more preferably 2 minutes to 12 hrs, even more preferably 3 minutes to 6 hrs, and most preferably 30 minutes to 2 hrs.

The reaction is preferably carried under nitrogen or argon or other noble gas or another inert gas.

The inventive method of deprotecting trichloroethoxycarbonyl (TROC) in the reaction is not only useful for preparation of cabazitaxel, but also for preparation of docetaxel and paclitaxel.

Preparation of Compound III (Step d)

The inventive method of the invention includes reacting compound IV with a base to obtain intermediate metallated compound VI

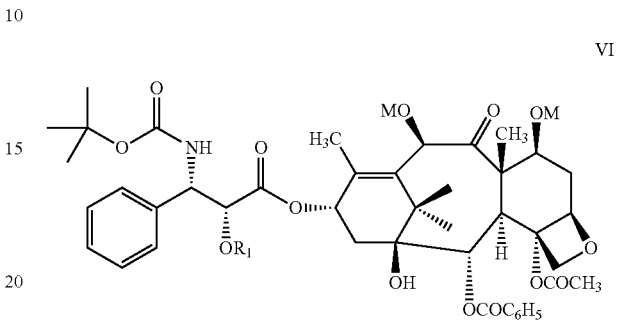

VI

M is a group IA, IIA, IIIA, IVA, VA, VIA metal or transition metal, zinc or calcium In the method of the invention, the base is an inorganic base metal base or organic base metal base.

Preferably the base is sodium methoxide, sodium amide, sodium hydride, lithium n-butyl, lithium bi(trimethyl silyl) amino or sodium hexamethyl bisilyl amino.

The reaction of the invention is typically carried out at −100 to 75 degrees C., preferably −10 to 50 degrees C. and more preferably 5 to 10 degrees C.

The reaction time for the invention can be 1 minute to 24 hrs, or more preferably 2 minutes to 12 hrs, even more preferably 3 minutes to 6 hrs, and most preferably 30 minutes to 2 hrs.

The reaction is preferably carried in the absence of water and oxygen, under nitrogen or argon or other noble gas or another inert gas.

Compound VI is subsequently reacted with methyl iodide (MeI) or dimethyl sulfate (Me)$_2$SO$_4$ to obtain compound III via a methylation reaction, replacing the metals M with methyl groups.

Preparation of Cabazitaxel from Compound III (Step e)

Compound III is deprotected at the R1 position preferably in aqueous solution having pH 1 to 9.

Preferably the above R1 deprotection reaction is in acid solution wherein the acid is formic acid, acetic acid, hydrofluoric acid, hydrochloric acid, p-methylphenyl sulfonic acid or a mixture thereof. Preferably the acid is hydrochloric acid or hydrofluoric acid, the solution is aqueous solution, organic solution or mixed aqueous-organic solution.

In a method of the invention, the above R1 deprotection reaction is carried out at −50 to 100 degrees C., preferably −30 to 60 degrees C., or most preferably −10 to 20 degrees C.

The R1 deprotection reaction is carried out for example for 0.5 hr to 80 hrs, preferably 1 hr to 60 hrs, or more preferably 2 hrs to 50 hrs.

Preparation of Docetaxel Directly from Compound IV

An equivalent R1 deprotection reaction as step (e) above can be used to prepare docetaxel directly from compound IV. Preferably the deprotection is carried out in aqueous solution having pH 1 to 9.

Preferably the above deprotection reaction is in acid solution wherein the acid is formic acid, acetic acid, hydrofluoric acid, hydrochloric acid, p-methylphenyl sulfonic acid or a mixture thereof. Preferably the acid is hydrochloric acid or hydrofluoric acid, the solution is aqueous solution, organic solution or mixed aqueous-organic solution.

In a method of the invention, the above deprotection reaction is carried out at −50 to 100 degrees C., preferably −30 to 60 degrees C., or most preferably −10 to 20 degrees C.

The deprotection reaction is carried out for example for 0.5 hr to 80 hrs, preferably 1 hr to 60 hrs, or more preferably 2 hrs to 50 hrs.

9-DHB Synthetic Routes

The above methods start from the taxane compound 10-deacetylbaccatin (10-DAB), derived from *Taxus* plant species. In addition, it is possible to adopt the same or equivalent synthetic strategies to produce cabazitaxel starting from a different taxoid starting material, namely 9-dihydro-13-acetylbaccatin III (9-DHB), present in another *Taxus* species, namely the Canadian yew (*Taxus Canadensis*).

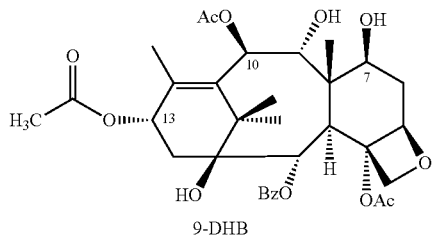
9-DHB

Figure 2:
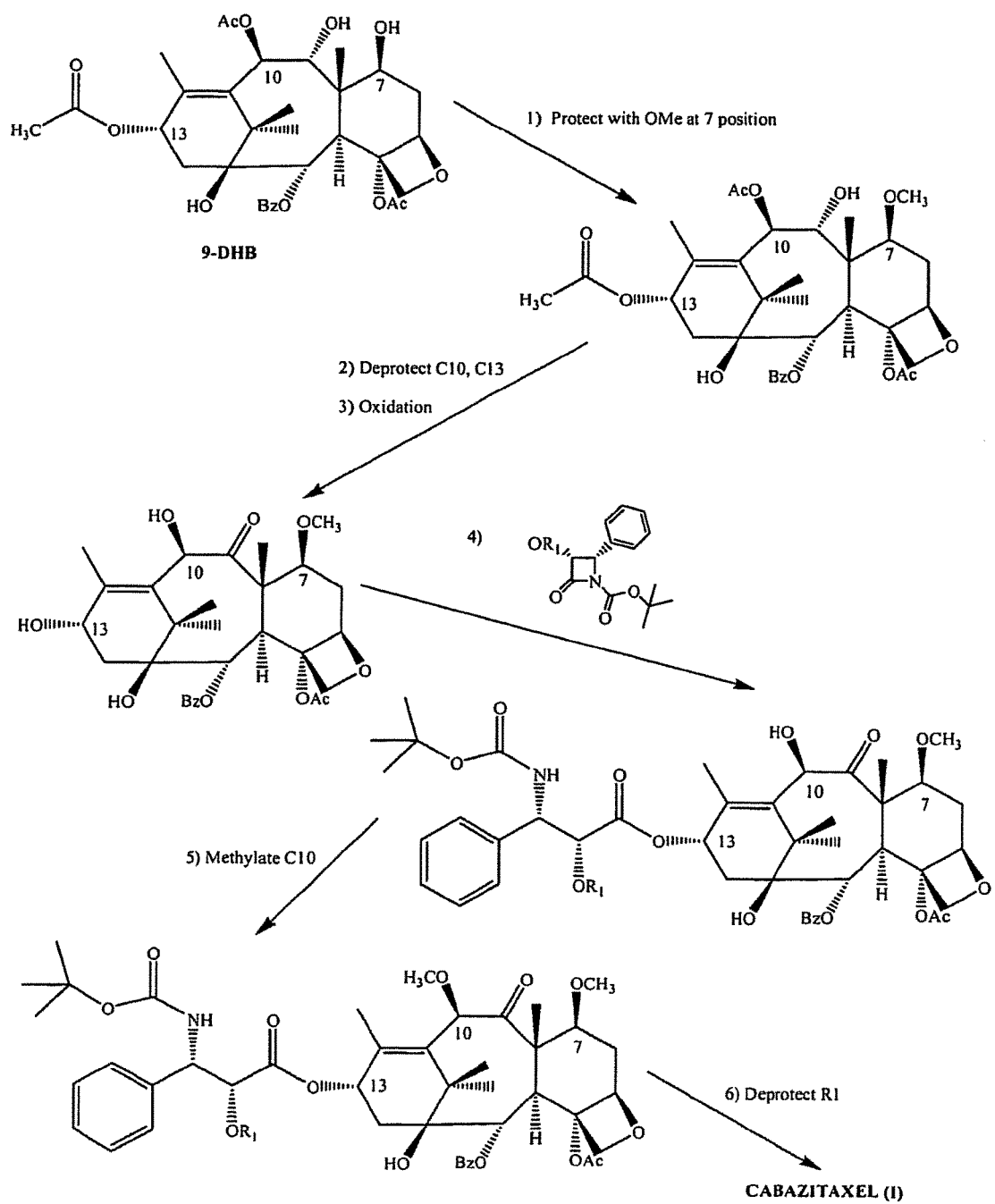
FIG. 2 depicts a second method of preparing cabazitaxel according to the invention.

The equivalent 9-DHB synthetic methods may be summarized as follows, and are depicted in FIG. 2:
 1. Starting from 9-DHB, protect the 7 position with methoxy (OMe);
 2. Deprotect the resultant 7-protected 9-DHB at the C10 and C13 positions to yield 7-OMe-10,13-deacetyl-9DHB;
 3. Oxidize at 9-position to give 7-OMe-10DAB, i.e introduce a keto group at the 9-position;
 4. Couple the 7-protected 10-DAB analogue at the 13 position to a phenylisoserine side-chain precursor (a beta-lactam) protected by a suitable hydroxy protecting group R1 at the 2'-position such that the resulting 7-protected C-13 substituted taxane intermediate has an R1 hydroxy protecting group at the 2'-position on the phenylisoserine side chain;
 5. Methylate as described above (step d) for the 10-DAB pathway at the 10 position to provide novel ester III; and
 6. Deprotect the R1 group as described above (step e) for the 10-DAB pathway to yield cabazitaxel (I).

Alternatively, in the 9-DHB procedure immediately above, steps (3) and (4) may be performed in the opposite order, namely firstly coupling the phenylisoserine chain at the 13 position, then oxidizing the 9 position.

Furthermore, one could reverse the order of steps (1) and (2), namely firstly deprotecting at the 10 and 13 positions to provide 7,10,13-hydroxy-9DHB, then selectively methylating at the 7 position to yield 7-OMe-10,13 deacetyl-9DHB. Then, the steps (3) to (6) are carried out as described above.

Figure 3:
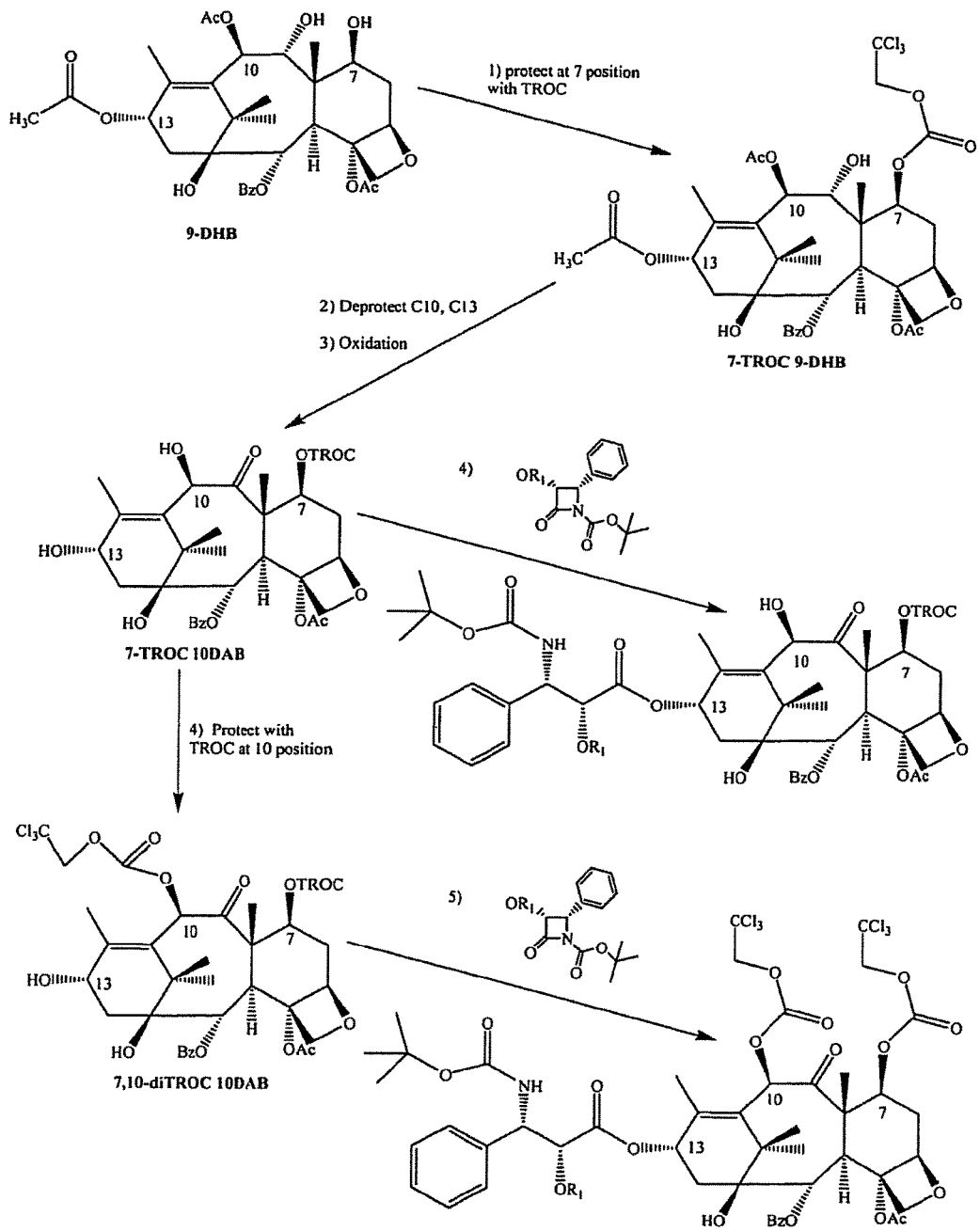
FIG. 3 depicts further reaction schemes according to the invention.

FIG. 3 depicts a further synthetic scheme of the invention, again using the starting material 9DHB.

In the FIG. 3 scheme, 9DHB is firstly protected using a protecting group TROC at the 7 position. This is equivalent to step (a) explained above. The 7-TROC protected 9DHB is then deprotected at the C10 and C13 positions, and is oxidized to provide the 7-TROC protected 10DAB equivalent compound.

7-TROC 10DAB can then be coupled to its phenylisoserine side chain as explained above, to yield a mono-TROC protected docetaxel analogue.

Alternatively, the 7-TROC 10DAB may be further protected with TROC to yield 7,10-diTROC 10DAB which is labeled as protected taxane intermediate V above. Compound V may then be used in the pathways explained above in connection with FIG. 1, to produce cabazitaxel or docetaxel.

Figure 4:
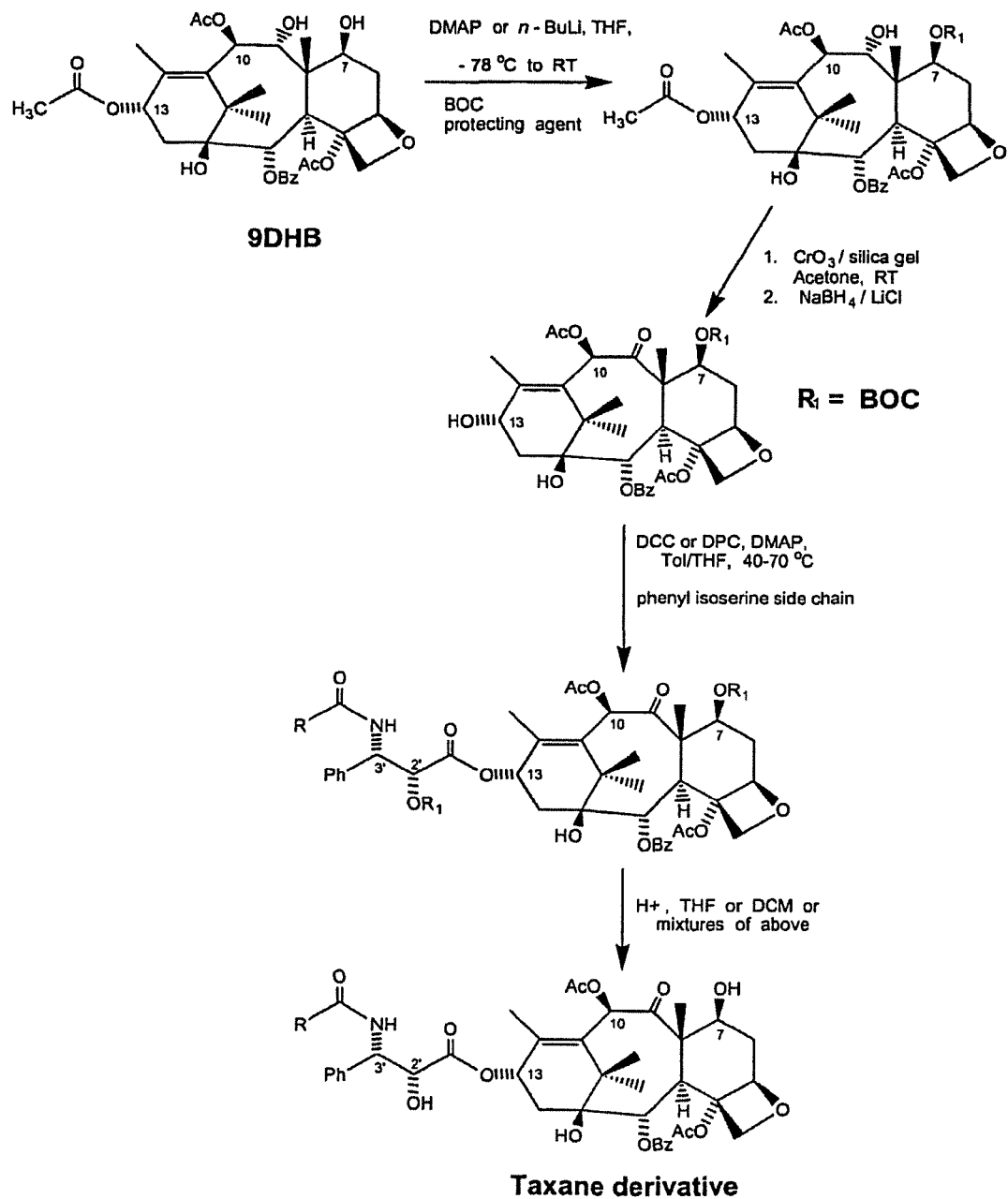
FIG. 4 depicts a prior art synthesis of taxane derivatives starting from 9-DHB.

The necessary reaction conditions for "protection", "deprotection", "oxidation" and "side chain coupling" to manufacture taxane intermediates starting from 9-DHB are known in the art of taxane molecule synthesis, for example in EP 2 003 124 A1. Nevertheless, FIG. 4 presents a typical synthesis for information.

The invention has several advantages. The invention provides a new, simple, easy to operate method of synthesizing cabazitaxel, paclitaxel and docetaxel. The method has fewer steps, mild reaction conditions and high purity of the reaction solution. Work-up treatment is easy and the intermediates and product are obtained simply by crystallization. This simplifies the operation and the requirements for equipment and decreases the production cost. Further, the schemes described herein yield a stable solid intermediate which benefits the quality control of both intermediates and final product, especially during industrial production.

The invention is illustrated by the following examples. These examples only illustrate the invention but do not restrict the invention.

EXAMPLES

The following acronyms are used in the examples: TES=triethylsilyl; TROC=trichloroethoxycarbonyl, also known as trichloroethyloxycarbonyl, defined by the formula $CCl_3CH_2OC(O)-$; TBS=t-Butyldimethylsilyl; and THP=tetrahydropyran.

Example 1

Comparative

Pour 80 ml acetic acid and 12 g active zinc powder into a reaction container, stirring evenly, increase temperature to 60-70 degrees C., add 5 g of 2'-TBS-7,10-TROC-docetaxel, and stir for 5 hrs until TLC shows the reaction completion. After filtering, add 80 ml of ethyl acetate and 80 ml of water into the filter liquor, extract, wash the organic layer with 50 ml of water, saturated $NaHCO_3$ (50 ml×2), saturated NaCl (50 ml). Then dry with anhydrous $Na_2SO_4$. Filter and then evaporate the solution to gain white solid 2'-TBS-Docetaxel 2.5 g (yield 81%).

MS (m/z): 972 (M+Na). $_1$HNMR (500 MHz) δ 0.31 (6H, m), 0.92 (9H, m), 1.13 (3H, s), 1.30 (12H, m), 1.72 (7H, m), 1.92 (4H, m), 2.18 (1H, m), 2.35 (1H, m), 2.61 (4H, m), 3.95 (1H, d), 4.21 (3H, m), 4.28 (1H, d), 4.54 (1H, s), 4.97 (1H, d), 5.21 (1H, s), 5.27 (1H, m), 5.50 (1H, m), 5.70 (1H, d), 6.31 (1H, t), 7.29 (2H, m), 7.37 (2H, t), 7.59 (1H, t), 8.11 (1H, d),

Example 2

At 35 to 40 degrees C., add 50 ml of methanol, 10 g of active zinc powder, 50 ml of water and 10 g of $NH_4Cl$ into a 100 ml reaction container. Stirring evenly, then add 5 g of 2'-TES-7,10-TROC-docetaxel. Stir 4 hrs until TLC shows reaction completed. After filtering, add 80 ml of ethyl acetate, 80 ml of water into filter liquor, after extracting wash the organic layer with water (50 ml), saturated $NaHCO_3$ (50 ml×2), saturated NaCl (50 ml), dry with non-aqueous $Na_2SO_4$, filter and evaporate the solution to obtain white solid, 2.8 g of 2'-TES-docetaxel (yield 90%).

MS (m/z): 972 (M+Na). $_1$HNMR (500 MHz) δ 0.39 (6H, m), 0.78 (9H, m), 1.13 (3H, s), 1.30 (12H, m), 1.72 (7H, m), 1.92 (4H, m), 2.18 (1H, m), 2.35 (1H, m), 2.61 (4H, m), 3.95 (1H, d), 4.21 (3H, m), 4.28 (1H, d), 4.54 (1H, s), 4.97 (1H, d), 5.21 (1H, s), 5.27 (1H, m), 5.50 (1H, m), 5.70 (1H, d), 6.31 (1H, t), 7.29 (2H, m), 7.37 (2H, t), 7.59 (1H, t), 8.11 (1H, d),

Example 3

At room temperature add 50 ml of ethanol, 10 g of active zinc powder and 10 g of $NH_4Cl$ into a 100 ml reaction container. Stirring evenly, add 5 g of 2'-(1-ethoxyethyl)-7,10-TROC-docetaxel. Stir 1 hr until TLC shows reaction completion, filter and evaporate the filter liquor to obtain white solid, 2'-(1-ethoxyethyl)-docetaxel, 3.1 g, (yield 88%).

MS (m/z): 902 (M+Na). $_1$HNMR (500 MHz) δ 1.13 (6H, m), 1.30 (15H, m), 1.72 (7H, m), 1.92 (4H, m), 2.18 (1H, m), 2.35 (1H, m), 2.61 (4H, m), 3.48 (2H, m), 3.95 (1H, d), 4.21 (3H, m), 4.28 (1H, d), 4.37 (1H, m), 4.54 (1H, s), 4.97 (1H, d), 5.21 (1H, s), 5.27 (1H, m), 5.50 (1H, m), 5.70 (1H, d), 6.31 (1H, t), 7.29 (2H, m), 7.37 (2H, t), 7.59 (1H, t), 8.11 (1H, d),

Example 4

At room temperature add 50 ml of methanol, 8 g of active zinc powder and 8 g of $NH_4Cl$ into a 100 ml reaction container. Stirring evenly, add 5 g of 2'-THP-7,10-TROC-docetaxel. Stir 1 hr until TLC shows reaction completion, filter, evaporate the filter liquor to obtain white solid 3.3 g of 2'-THP-docetaxel. (yield 91%).

$_1$HNMR (500 MHz) δ 1.15 (6H, m), 1.42 (15H, m), 1.82 (7H, m), 1.96 (6H, m), 2.28 (5H, m), 2.38 (3H, m), 2.69 (5H, m), 3.38 (4H, m), 3.88 (1H, d), 4.25 (3H, m), 4.26 (1H, d), 4.39 (1H, m), 4.54 (1H, s), 4.97 (1H, d), 5.21 (1H, s), 5.32 (1H, m), 5.50 (1H, m), 5.72 (1H, d), 6.32 (1H, t), 7.39 (2H, m), 7.39 (2H, t), 7.61 (1H, t), 8.11 (1H, d),

Example 5

At room temperature add 50 ml of methanol, 8 g of active zinc powder and 8 g of $NH_4Cl$ into a 100 ml reaction container. Stirring evenly, add 5 g of 2'-TES-7,10-TROC-docetaxel. Stir 1 hr, TLC shows reaction completion, filter, evaporate to obtain white solid 3.0 g of 2'-TES-docetaxel (yield 97%).

The examples 1-5 show that the yield when deprotecting TROC according to the invention (example 2-5) is improved compared to current technology (example 1). Example 1 is a prior art-type acetic acid deprotection, and as well as suffering from worse yield, also has more steps than the inventive method.

Example 6

Add 50 ml of tetrahydrofuran and 5 g of 2'-TES-docetaxel in 100 ml reaction container, stirring evenly, decrease temperature to −10 to −5 degrees C., add 2.5 ml of 30% n-butyl lithium solution dropwise into a 100 ml reaction container, add 0.8 ml of methyl iodide dropwise at −10 to −5 degrees C. and stir 1 hr. After TLC shows reaction completed, add 80 ml of ethyl acetate and 80 ml of saturated $NH_4Cl$ solution into the reaction solution. After extracting, wash the organic layer with saturated $NH_4Cl$ (50 ml×2), saturated NaCl (50 ml), then dry with non-aqueous $Na_2SO_4$, filter and evaporate the solution to obtain a light yellow viscous solid, 4.3 g of 2'-TES-cabazitaxel (yield 85%).

$_1$HNMR (500 MHz) δ 0.38 (6H, m), 0.79 (9H, m), 1.2~1.3 (16H, m), 1.60 (2H, m), 1.72 (3H, m), 1.96 (3H, m), 2.04 (1, s), 2.35 (1H, m), 2.53 (3H, s), 3.31 (3H, s), 3.46 (3H, s), 3.88 (2H, m), 4.11 (1H, m), 4.19 (1H, d), 4.32 (1H, d), 4.55 (1H, s), 4.81 (1H, s), 4.97 (1H, d), 5.29 (1H, m), 5.50 (1H, m), 5.66 (1H, d), 6.31 (1H, t), 7.29 (4H, m), 7.37 (2H, t), 7.48 (2H, t), 7.59 (1H, t), 8.11 (2H, d),

Example 7

Add 50 ml of methyl iodide and 5 g of 2'-TBS-docetaxel into a 100 ml reaction container, stirring evenly, decrease temperature to −10 degrees C. to −5 degrees C. Add 0.26 g of 50% NaH dropwise. Stir at −10 degrees C. to −5 degrees C. for 1 hr. TLC shows the reaction completion. Add 80 ml of ethyl acetate and 80 ml of saturated $NH_4Cl$ solution, extract, wash the organic layer with saturated $NH_4Cl$ (50 ml×2), saturated NaCl (50 ml), dry with anhydrous $Na_2SO_4$, filter and evaporate the solution to obtain a light yellow viscous solid 4.4 g of 2'-TBS-cabazitaxel (yield 87%).

$_1$HNMR (500 MHz) δ 0.38 (6H, s), 0.95 (9H, s), 1.2~1.3 (16H, m), 1.60 (2H, m), 1.72 (3H, m), 1.96 (3H, m), 2.04 (1H, s), 2.35 (1H, m), 2.53 (3H, s), 3.31 (3H, s), 3.46 (3H, s), 3.88 (2H, m), 4.11 (1H, m), 4.19 (1H, d), 4.32 (1H, d), 4.55 (1H, s), 4.81 (1H, s), 4.97 (1H, d), 5.29 (1H, m), 5.50 (1H, m), 5.66 (1H, d), 6.31 (1H, t), 7.29 (4H, m), 7.37 (2H, t), 7.48 (2H, t), 7.59 (1H, t), 8.11 (2H, d),

Example 8

Add 50 ml of methyl iodide and 5 g of 2'-TES-docetaxel into a 100 ml reaction container, stirring evenly, decrease temperature to −10 degrees C. to −5 degrees C. Add 0.26 g of 50% NaH dropwise. Stir at −10 degrees C. to −5 degrees C. for 1 hr. TLC shows the reaction completion. Add 80 ml of ethyl acetate and 80 ml of saturated $NH_4Cl$ solution, extract, wash the organic layer with saturated $NH_4Cl$ (50 ml×2), saturated NaCl (50 ml), dry with anhydrous $Na_2SO_4$, filter and evaporate the solution to obtain a light yellow viscous solid 4.3 g of 2'-TES-cabazitaxel (yield 87%).

Example 9

Add 50 ml of methyl iodide and 5 g of 2'-THP-docetaxel into a 100 ml reaction container, stirring evenly, decrease temperature to −10 degrees C. to −5 degrees C. Add 0.26 g of 50% NaH dropwise. Stir at −10 degrees C. to −5 degrees C. for 1 hr. TLC shows the reaction completion. Add 80 ml of ethyl acetate and 80 ml of saturated $NH_4Cl$ solution, extract, wash the organic layer with saturated $NH_4Cl$ (50 ml×2), saturated NaCl (50 ml), dry with non-aqueous $Na_2SO_4$, filter and evaporate the solution to obtain a light yellow viscous solid 4.3 g of 2'-THP-cabazitaxel (yield 87%).

$_1$HNMR (500 MHz) δ 1.15 (6H, m), 1.42 (15H, m), 1.82 (7H, m), 1.96 (6H, m), 2.28 (5H, m), 2.38 (3H, m), 2.69 (5H, m), 3.31 (6H, m), 3.46 (3H, s), 3.88 (1H, d), 4.25 (3H, m), 4.26 (1H, d), 4.39 (1H, m), 4.54 (1H, s), 4.97 (1H, d), 5.21 (1H, s), 5.32 (1H, m), 5.50 (1H, m), 5.72 (1H, d), 6.32 (1H, t), 7.39 (2H, m), 7.39 (2H, t), 7.61 (1H, t), 8.11 (1H, d),

Example 10

Add 50 ml of tetrahydrofuran, 1 ml of dimethyl sulfate and 5 g of 2'-THP-docetaxel in a 100 ml reaction container, stirring evenly, decrease temperature to −10 to −5 degrees C., add 0.26 g of 30% sodium methoxide in methanol solution dropwise, stir at −10 to −5 degrees C. for 1 hr. TLC shows reaction completed. Add 80 ml of ethyl acetate and 80 ml of saturated $NH_4Cl$ solution into the reaction solution, extract, wash organic layer with saturated $NH_4Cl$ (50 ml×2), saturated NaCl (50 ml), dry with anhydrous $Na_2SO_4$, filter and evaporate the solution to obtain light yellow viscous solid, 45.1 g of 2'-THP-cabazitaxel (yield 90%).

Example 11

2'-(1-ethoxy-ethyl)-cabazitaxel preparation is the same as Example 10 (yield 88%).
$_1$HNMR (500 MHz) δ 1.13 (6H, m), 1.30 (15H, m), 1.72 (7H, m), 1.92 (4H, m), 2.18 (1H, m) 2.35 (1H, m) 2.61 (4H, m), 3.31 (3H, s), 3.46 (5H, m), 3.95 (1H, d), 4.21 (3H, m), 4.28 (1H, d), 4.37 (1H, m), 4.54 (1H, s), 4.97 (1H, d), 5.21 (1H, s), 5.27 (1H, m), 5.50 (1H, m), 5.70 (1H, d), 6.31 (1H, t), 7.29 (2H, m), 7.37 (2H, t), 7.59 (1H, t), 8.11 (1H, d), Example 12

Dissolve 100 g of 2'-THP-cabazitaxel in 1730 ml of HOAc/$H_2O$/THF (3:1:1), under $N_2$ atmosphere, increase temperature to 50 degrees C. and stir 4 hrs. Then cool to room temperature. Add 2 L of ethyl acetate, 2 L of $H_2O$, stir, separate layers, wash organic layer with saturated $NaHCO_3$ (3 L×2), saturated NaCl (3 L), dry with $Na_2SO_4$. Concentrate to obtain white 77.8 g of cabazitaxel (yield 83%).
MS (m/z): 859 (M+Na). $_1$HNMR (500 MHz) δ 1.21 (6H, d), 1.36 (9H, s), 1.59 (1H, s), 1.64 (1H, s), 1.79 (1H, m), 1.87 (3H, s), 2.27 (2H, m), 2.35 (3H, m), 2.69 (1H, m), 3.30 (3H, s), 3.45 (3H, s), 3.85 (2H, m), 4.16 (1H, d), 4.29 (1H, d), 4.62 (1H, bs), 4.79 (1H, s), 5.29 (1H, m), 5.42 (1H, d), 5.62 (1H, d), 6.21 (1H, t), 7.2~7.4 (6H, m), 7.48 (2H, t), 7.59 (1H, t), 8.11 (2H, d), Example 13

Dissolve 100 g of 2'-TES-cabazitaxel in 10 L of acetonitrile, add 650 ml of pyridine, decrease temperature to −8 degrees C., add 1.5 L of hydrofluoric acid dropwise while keeping reaction temperature at or below −3 degrees C. (about 90 minutes). After addition is complete, keep at 0 degrees C. for 22 hrs.
Add 10 L of ethyl acetate to the reaction solution for dilution, then wash with 1 N hydrochloric acid, extract aqueous layer with 10 L non-aqueous ethyl acetate, combine organic layers, wash with saturated $NaHCO_3$ (10 L×5), saturated NaCl (3.5 L×1). Dry with anyhydrous $Na_2SO_4$ then concentrate under reduced pressure (<35 degrees C.) to dry to obtain 85.1 g of cabazitaxel (yield 97%).

Example 14

Dissolve 100 g of 2'-(1-ethoxyethyl)-cabazitaxel in tetrahydrofuran, add 1 L of ethanol, decrease temperature to −8 degrees C. Add 2N hydrochloric acid (200 ml) dropwise, while keeping the reaction temperature at or below −3 degrees C. (about 90 minutes). After addition, keep at 0 degrees C. for 22 hrs.
Add 24 L of ethyl acetate into the reaction solution to dilute, then wash with 1 N hydrochloric acid (20 L×2), extract aqueous phase with 10 L anhydrous ethyl acetate, combine organic layers, wash with saturated $NaHCO_3$ (20 L×5), saturated NaCl (7.5 L×1). Dry with anhydrous $Na_2SO_4$ then concentrate under reduced pressure (<35 degrees C.) to dry to obtain 83.2 g of cabazitaxel (yield 95%).

Example 15

Synthesis method of cabazitaxel from 2'-TBS-cabazitaxel is same as Example 13.

Example 16

Synthesis method of cabazitaxel from 2'-TES-docetaxel is the same as Example 13.
MS (m/z): 830 (M+Na). 1H NMR ($CDCl_3$, 500 MHz): δ 8.12 (d, 2H), 7.63 (t, 1H), 7.51 (t, 2H), 7.32~7.35 (m, 5H), 6.19 (bt, 1H), 4.66 (d, 1H), 4.33 (d, 1H), 4.21 (m, 1H), 4.18 (d, 1H), 3.92 (d, 1H), 3.53 (s, 1H), 2.63 (m, 1H), 2.55 (m, 1H), 2.38 (s, 3H), 2.24 (m, 2H), 1.90 (s, 3H), 1.85 (m, 1H), 1.80 (s, 3H), 1.35 (m, 9H), 1.26 (s, 3H), 1.13 (s, 3H)

Example 17

Synthesis method of 2'-TES-taxol from 2'-TES-7-TROC-taxol is same as Example 2.
1H NMR (CDCl3, 500 MHz): δ 8.12 (d, 2H), 7.73 (d, 2H), 7.51 (t, 1H), 7.44 (m, 5H), 7.38 (m, 5H), 7.03 (d, 1H), 6.24 (s, 1H), 6.22 (bt, 1H), 5.78 (dd, 1H), 5.67 (d, 1H), 4.93 (bd, 1H), 4.79 (d, 1H), 4.39 (dd, 1H), 4.30 (d, 1H), 4.19 (d, 1H), 4.11 (dd, 1H), 3.79 (d, 1H), 3.67 (bs, 1H), 2.53 (ddd, 1H), 2.43 (bs, 1H), 2.38 (s, 3H), 2.31 (dd, 1H), 2.26 (dd, 1H), 2.23 (s, 3H), 2.03 (s, 2H), 1.86 (m, 1H), 1.74 (s, 3H), 1.67 (s, 3H), 1.22 (s, 3H), 1.14 (s, 3H), 0.85 (9H, m), 0.41 (6H, m).

Example 18

Synthesis method of taxol from 2'-TES-taxol is the same as Example 13.
MS (m/z): 876 (M+Na). 1H NMR ($CDCl_3$, 500 MHz): δ 8.12 (d, 2H), 7.73 (d, 2H) 7.51 (t, 1H), 7.44 (m, 5H), 7.38 (m, 5H), 7.03 (d, 1H), 6.24 (s, 1H), 6.22 (bt, 1H), 5.78 (dd, 1H), 5.67 (d, 1H), 4.93 (bd, 1H), 4.79 (d, 1H), 4.39 (dd, 1H), 4.30 (d, 1H), 4.19 (d, 1H), 4.11 (dd, 1H), 3.79 (d, 1H), 3.67 (bs, 1H), 2.53 (dd, 1H), 2.43 (bs, 1H), 2.38 (s, 3H), 2.31 (dd, 1H), 2.26 (dd, 1H), 2.23 (s, 3H), 2.03 (s, 2H), 1.86 (m, 1H), 1.74 (s, 3H), 1.67 (s, 3H), 1.22 (s, 3H), 1.14 (s, 3H).

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A method of preparing a taxane product compound from a protected taxane intermediate, the method comprising reacting the protected taxane intermediate with a reducing agent and a Lewis acid wherein the protected taxane intermediate has the formula V:

V

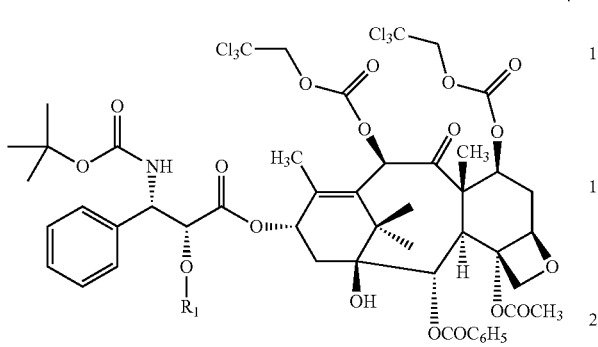

and the taxane compound has the formula IV,

IV

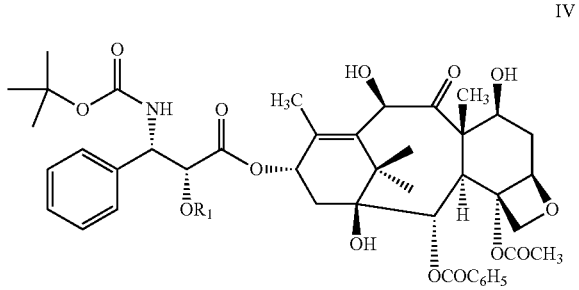

the method further comprising:
a.) reacting the taxane compound of formula IV

IV

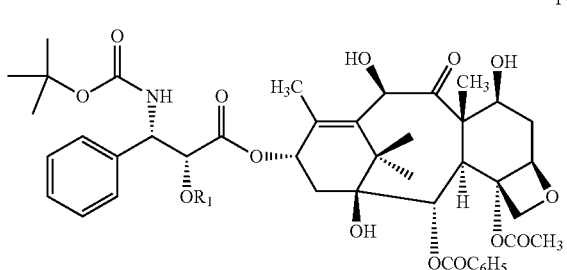

with a strong base to obtain a corresponding metallated compound VI

VI

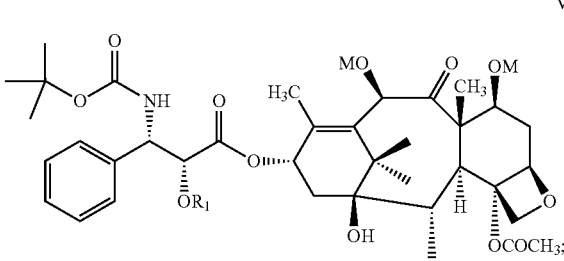

and
b.) reacting the metallated compound VI with methyl iodide or dimethyl sulphate to obtain compound III;

III

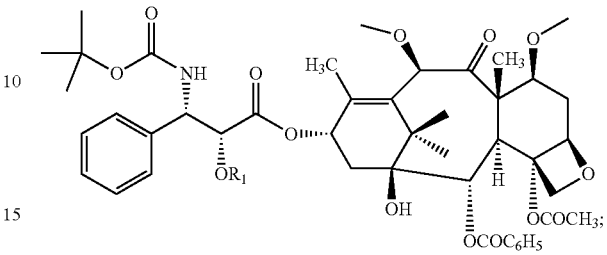

wherein R1 is a hydroxy protecting group; and
wherein M is selected from the group consisting of a IA, IIA, IIIA, IVA, VA, VIA group element or a transition metal, zinc, and calcium.

2. The method of claim 1, wherein the strong base is selected from the group consisting of sodium methoxide, sodium amide, sodium hydride, n-butyl-lithium, lithium bi(trimethyl silyl)amino and sodium hexamethyl bisilyl amino.

3. The method of claim 1, further comprising deprotecting the R1 protecting group from compound III

III

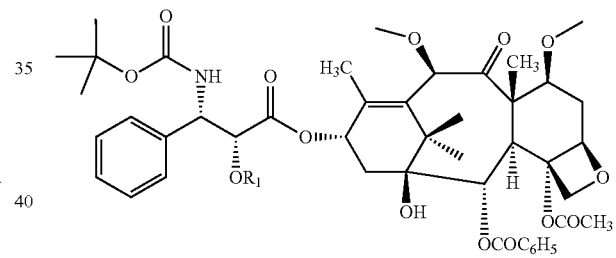

to obtain cabazitaxel

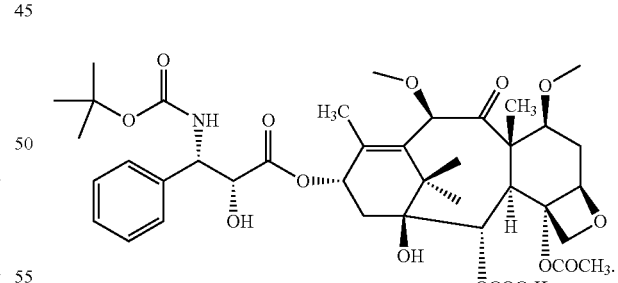

4. The method of claim 3, wherein the method is carried out by deprotecting the protecting group R1 in acid solvent, the acid being selected from formic acid, acetic acid, hydrofluoric acid, hydrochloric acid, p-methyl-benzene monosulfonic acid, and mixtures thereof.

5. The method of claim 1, wherein M is sodium, potassium, lithium, zinc, or calcium.

6. The method of claim 2, wherein the strong base is selected from the group consisting of sodium hydride and n-butyl-lithium.

7. The method of claim 4, wherein the acid is hydrochloric acid or hydrofluoric acid, and wherein the solvent is water, organic solvent, or organic solvent with water.

\* \* \* \* \*